(12) United States Patent
Strommer et al.

(10) Patent No.: US 10,610,693 B2
(45) Date of Patent: Apr. 7, 2020

(54) BATTERY AND ELECTRONICS INTEGRATION IN A FLEXIBLE IMPLANTABLE MEDICAL DEVICE

(71) Applicant: NewPace Ltd., Caesarea (IL)

(72) Inventors: Gera Strommer, Haifa (IL); Avi Broder, Petach Tikva (IL); Moti Mocha, Beit Dagan (IL); Robert S. Fishel, Delray Beach, FL (US); Nahum Natan, Tel Aviv (IL)

(73) Assignee: NewPace Ltd., Caesarea ( * ) Notice: Subject to any disclaimer, the term of this patent is extended or adjusted under 35 U.S.C. 154(b) by 158 days.

(21) Appl. No.: 15/822,792

(22) Filed: Nov. 27, 2017

(65) Prior Publication Data
US 2018/0078774 A1 Mar. 22, 2018

Related U.S. Application Data

(63) Continuation-in-part of application No. 14/904,333, filed as application No. PCT/IL2014/050629 on Jul. 11, 2014, now abandoned.
(Continued)

(51) Int. Cl.
*A61N 1/375* (2006.01)
*A61N 1/36* (2006.01)
(Continued)

(52) U.S. Cl.
CPC .......... *A61N 1/3752* (2013.01); *A61B 5/0031* (2013.01); *A61B 5/076* (2013.01);
(Continued)

(58) Field of Classification Search
CPC .. H05K 1/028; H05K 1/189; H05K 2201/042; A61N 1/375; A61N 1/3758; A61N 1/39; A61N 1/3956
See application file for complete search history.

(56) References Cited

U.S. PATENT DOCUMENTS

| 5,448,511 A | 9/1995 | Paurus et al. |
| 5,645,586 A | 7/1997 | Meltzer |

(Continued)

FOREIGN PATENT DOCUMENTS

| CN | 1762510 A | 4/2006 |
| CN | 102665371 A | 9/2012 |

(Continued)

OTHER PUBLICATIONS

Extended European Search Report dated May 18, 2017 for European Application No. 14822324.1 (11 Pages).
(Continued)

*Primary Examiner* — Allen Porter
(74) *Attorney, Agent, or Firm* — Nathan & Associates; Menachem Nathan

(57) ABSTRACT

An encapsulation configuration for electronic components in a flexible implantable medical device, including at least one set of folded circuit boards and a filler material, the set of folded circuit boards including a plurality of circuit boards and a plurality of connection cables, each one of the circuit boards including at least one electronics component, each one of the circuit boards having a generally rectangular shape, the connection cables electrically coupling adjacent ones of the circuit boards and the circuit boards being folded over one another in a pleated manner, the filler material surrounding the set of folded circuit boards, the filler material and the set of folded circuit boards together having a cylindrical shape, the set of folded circuit boards being positioned lengthwise in the cylindrical shape and the electronics component being positioned on the set of folded circuit boards to achieve optimal volume consumption in the electronics encapsulation.

16 Claims, 10 Drawing Sheets

Related U.S. Application Data

(60) Provisional application No. 61/844,880, filed on Jul. 11, 2013.

(51) Int. Cl.
 A61B 5/07 (2006.01)
 A61B 5/00 (2006.01)
 A61N 1/378 (2006.01)

(52) U.S. Cl.
 CPC ....... *A61N 1/36125* (2013.01); *A61N 1/3758* (2013.01); *A61N 1/37512* (2017.08); *A61B 2560/0418* (2013.01); *A61N 1/3756* (2013.01); *A61N 1/3787* (2013.01)

(56) References Cited

U.S. PATENT DOCUMENTS

| | | |
|---|---|---|
| 6,245,092 B1 | 6/2001 | Schaldach, Jr. |
| 6,658,296 B1 | 12/2003 | Wong et al. |
| 7,211,884 B1 * | 5/2007 | Davis ................ A61B 5/0031 257/685 |
| 7,655,348 B2 | 2/2010 | Nanno et al. |
| 7,656,673 B1 | 2/2010 | Fries et al. |
| 7,985,500 B2 | 7/2011 | Root et al. |
| 8,361,644 B2 | 1/2013 | Kane et al. |
| 2003/0048621 A1 | 3/2003 | Blood et al. |
| 2004/0176817 A1 | 9/2004 | Wahlstrand et al. |
| 2004/0260372 A1 | 12/2004 | Canfield et al. |
| 2006/0212087 A1 | 9/2006 | Haller et al. |
| 2006/0217779 A1 | 9/2006 | Ransbury et al. |
| 2007/0243456 A1 | 10/2007 | Ahn et al. |
| 2008/0021281 A1 | 1/2008 | Fujimori |
| 2008/0077219 A1 | 3/2008 | Williams et al. |
| 2008/0093110 A1 | 4/2008 | Bagung |
| 2008/0167702 A1 | 7/2008 | Ransbury et al. |
| 2009/0266573 A1 | 10/2009 | Engmark et al. |
| 2010/0304197 A1 | 12/2010 | Bhardwaj et al. |
| 2010/0326703 A1 | 12/2010 | Gilad et al. |
| 2012/0121963 A1 | 5/2012 | Kwon et al. |
| 2012/0202101 A1 | 8/2012 | Ueda |
| 2016/0228716 A1 | 8/2016 | Schmidt et al. |
| 2016/0296760 A1 | 10/2016 | Sahabi et al. |

FOREIGN PATENT DOCUMENTS

| | | |
|---|---|---|
| CN | 103118740 A | 5/2013 |
| EP | 2422842 A1 | 2/2012 |
| WO | 2005098994 A1 | 10/2005 |
| WO | 2007070717 A2 | 6/2007 |
| WO | 2012138782 A1 | 10/2012 |
| WO | 2014089299 A2 | 6/2014 |

OTHER PUBLICATIONS

International Search Report and Written Opinion of the International Searching Authority dated Nov. 5, 2014 for International Application No. PCT/IL2014/050629 (21 Pages).

Search Report of the State Intellectual Property Office for Chinese Application No. CN201480050355X (2 Pages).

* cited by examiner

BATTERY AND ELECTRONICS INTEGRATION IN A FLEXIBLE IMPLANTABLE MEDICAL DEVICE

RELATED APPLICATIONS

This application is a continuation-in-part of U.S. patent application Ser. No. 14/904,333, filed on Jan. 11, 2016, which is a national phase application of international application no. PCT/IL2014/050629, filed on Jul. 11, 2014, which claims priority to and the benefit of U.S. provisional patent application No. 61/844,880, filed Jul. 11, 2013. The entirety of each of these applications is incorporated herein by reference.

FIELD OF THE DISCLOSED TECHNIQUE

The disclosed technique relates to battery and electronics integration, in general, and to methods and systems for integrating a battery and electronics in flexible implantable medical devices as well as non-implanted medical devices, in particular.

BACKGROUND OF THE DISCLOSED TECHNIQUE

Implantable medical devices, such as pacemakers, defibrillators, brain stimulators, pain relief stimulators, sleep apnea stimulators, other stimulation devices and the like, require a source of power to function and operate. The source of power is usually a battery which is commonly contained in a can together with electronic components. The can is usually attached to another part of the implantable medical device which delivers some kind of therapy to a patient based on electrical impulses. As such devices may be typically worn or carried by patients for years or even decades the battery is usually implanted in the patient as part of the implantable medical device and is typically integrated into the device and not removable. When the battery dies and needs replacement, the patient must undergo surgery to remove the battery and replace it with a new one. In some devices, the entire device needs to be replaced as the battery is not a separately replaceable component. Thus the entire medical device requires replacement at the time of battery depletion. State of the art batteries used in such devices may last anywhere up to 5-7 years. However a patient who receives a pacemaker or defibrillator early in his or her life, such at age 40, and lives into his 80s may have to undergo multiple surgeries just to replace the battery of his pacemaker or defibrillator.

In many implantable medical devices, a part of the device, such as an electrical lead, may be positioned apart from the can containing the battery and electronics accordingly. For example, in prior art pacemakers, electrical leads which are used to both measure the heart's electrical activity and also provide electrical stimulation to the heart are placed in a different location than the can which houses the battery as well as electronics for controlling the pacemaker. The electrical leads are usually positioned within the heart, whereas the can may be positioned under the collarbone. Implanting the pacemaker requires major surgery as the electrical leads need to be positioned within the heart of a patient. In addition, an incision needs to be made to position the can in the body of the patient. At period intervals typically ranging from 5 to 7 years, the patient will have to undergo surgery to enable access to the can where the old battery is. The can is then replaced by removing it and inserting a new can, containing a new battery, in the patient. In addition, if any issues or problems ever occur with the electrical leads, the patient will again have to undergo major surgery to fix, repair or replace the electrical leads within the heart. It is noted that removing old electrical leads from the heart may be a complex medical procedure which can cause additional complications. In some cases, the old electrical leads may be left in the heart and new electrical leads are implanted next to the old ones. The can, which in prior art pacemakers is substantially bulky, is usually positioned in the body such that the patient will not be impaired with regard to physical movement and also to reduce any discomfort in the patient due to the positioning of the can. The patient though may suffer from discomfort in the tissue area that surrounds the can if a significant force is placed on the area, such as by getting hit in the area or falling on the area. In addition, thin patients or patients with limited amounts of subcutaneous tissue may also risk erosion of the device, for example the can, through the skin.

The integration of the power source with the other parts of an implantable medical device, such as the electrical leads, into a single unit in order that the can does not need to be separated from the electrical leads would make such an implantable medical device easier to handle and would simplify the surgery required to insert and remove the device in a patient. Such a unit could also include at least one electronic circuit or a series of electronic circuits as well as at least one capacitor. However replacing the battery of such a device every few years would still require the patient to undergo surgery. Such a device is described in U.S. Pat. No. 7,985,500 to Root et al., entitled "Method and apparatus for flexible battery for implantable device," which is directed to an apparatus for storing energy, the apparatus having a first portion comprising a flexible substrate containing a polymer electrolyte and a second portion adapted to provide a conformable housing surrounding the first portion. The apparatus is adapted to provide a source of energy to an implantable device. The apparatus with the implantable device forms a flexible implantable device capable of traversing the circulatory system of a body with minimal obstruction of flow within the circulatory system. In other embodiments of the apparatus to Root, the apparatus comprises at least one single cell contained within a flexible housing. Such an apparatus is adaptable to provide a source of energy to an implantable device. The apparatus can also contain both a sensor and a power source within the flexible housing. The housing can include an anchoring mechanism for anchoring the device during implantation within the body. The apparatus can also include a series of smaller battery cells attached by flexible conductive interconnects that are further contained within the conformable housing capable of traversing the circulatory system of the body.

What is needed then is an implantable medical device having a structure that incorporates the power source and electronic components, thus simplifying its placement in a patient, yet which also allows the power source to be easily replaced requiring only minor, less-invasive surgery. In addition, such a device should not impair a patient's movement at all and should cause no discomfort to the patient during their daily routine and activities.

SUMMARY OF THE DISCLOSED TECHNIQUE

It is an object of the disclosed technique to provide a novel electronics configuration for encapsulating the electronics in a flexible implantable medical device for achieving optimal volume consumption. In one aspect of the disclosed technique, there is thus provided an encapsulation configuration for electronic components in a flexible implantable medical device, including at least one set of folded circuit boards and a filler material. The set of folded circuit boards includes a plurality of circuit boards and a plurality of connection cables. Each one of the circuit boards includes at least one electronics component. Each one of the circuit boards has a generally rectangular shape and each one of the connection cables electrically couples adjacent ones of the circuit boards. The plurality of circuit boards is folded over one another in a pleated manner. The filler material surrounds the set of folded circuit boards, and together with the set of folded circuit boards has a cylindrical shape. The set of folded circuit boards is positioned lengthwise in the cylindrical shape and the electronics component is positioned on the set of folded circuit boards to achieve optimal volume consumption in the electronics encapsulation.

According to another aspect of the disclosed technique, there is thus provided an encapsulation configuration for electronic components in a flexible implantable cardioverter defibrillator (ICD) including at least two sets of folded circuit boards, a cylindrically shaped transformer and a filler material. Each one of the sets of folded circuit boards includes a plurality of circuit boards and a plurality of connection cables. Each one of the circuit boards includes at least one electronics component and has a generally rectangular shape. Each one of the connection cables electrically couples adjacent ones of the circuit boards. The plurality of circuit boards is folded over one another in a pleated manner. The transformer is positioned orthogonally between a first one of the sets of folded circuit boards and a second one of the sets of folded circuit boards. The filler material surrounds each one of the two sets of folded circuit boards, with the filler material, the transformer and the sets of folded circuit boards together having a cylindrical shape. The sets of folded circuit boards are positioned lengthwise in the cylindrical shape, orthogonally to the transformer. Each one of the electronics component is positioned on each one of the sets of folded circuit boards to achieve optimal volume consumption in the electronics encapsulation.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

Figure 1:
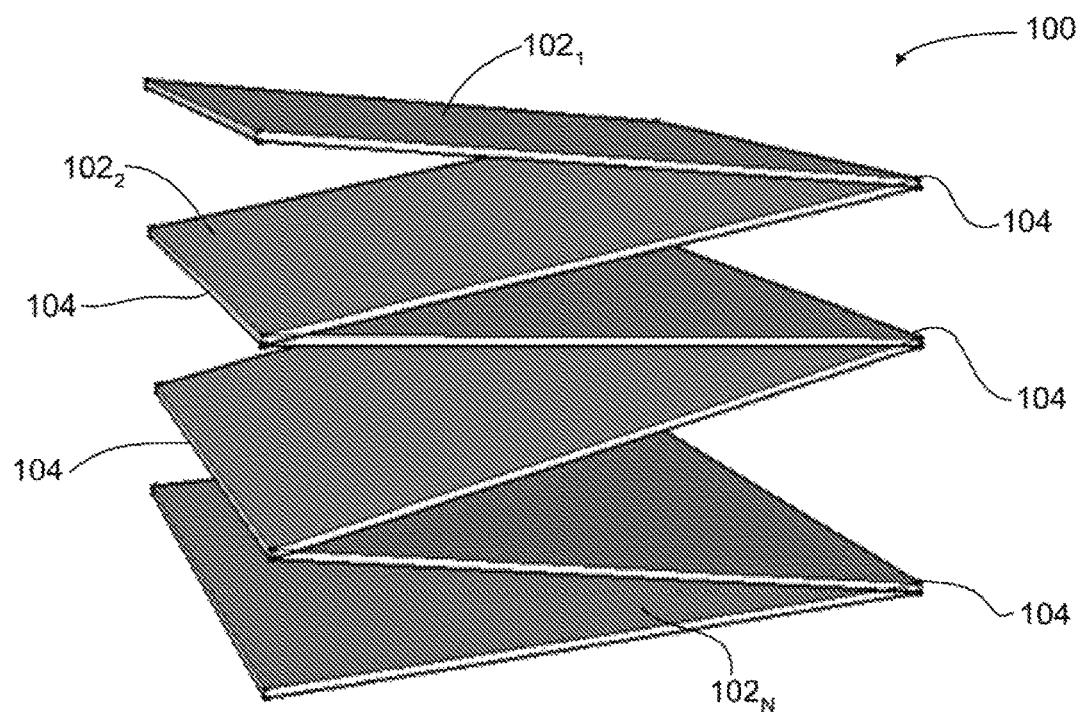
FIG. 1 is a schematic illustration of a first battery configuration, constructed and operative in accordance with an embodiment of the disclosed technique.

The disclosed technique overcomes the disadvantages of the prior art by providing a novel battery and electronics configuration, enabling the battery to be integrated into any implantable medical device having a flexible string-like or snake-like shape or form. The disclosed technique also provides for a novel encapsulation configuration for electronic components in an implantable medical device to be positioned and fitted compactly in such a device. The disclosed technique further provides for a novel battery which includes a plurality of flat high power single battery cells coupled together to form a battery unit. The disclosed technique can also be used in medical devices which are not implanted in a patient. The battery may be rigid or flexible, yet in either configuration, it enables the implantable medical device a significant amount of flexibility. The battery configuration enables the implantable medical device to include only one part which has a string-like shape, thus simplifying its insertion and placement within a patient. In addition, the battery configuration (along with the other components of an implantable medical device having a string-like shape) enables the battery to be easily and quickly removed and inserted after the implantable medical device has already been implanted in a patient without the need to remove the device itself, or without the need to remove a cover, frame or sheath positioned inside the patient which houses the implantable medical device. That being said, according to the disclosed technique, the whole implantable medical device can alternatively be removed through a small incision in the skin requiring only minor, less-invasive surgery due to its low profile and flexible string shape. The old battery of the device can then be removed and replaced with a new battery. The implantable medical device can then be reinserted into the patient via the small incision, which can then be simply sutured up. Thus the battery configuration of the disclosed technique enables the power source in an implantable medical device to be changed and replaced without requiring major surgery. It is noted that the battery configuration can be used in implantable medical devices which are inserted endovascularly as well as subcutaneously. In particular, according to the disclosed technique, implantable medical devices inserted subcutaneously having a flexible string shape can be easily removed and inserted due to the presence of a semi-rigid sheath which encapsulates the device, including its power source. As described below, the sheath can be left in the body of a patient, while the core of the device including the power source, the other parts of the implantable medical device or both can be easily removed. A core including a new power source or other components of the implantable medical device can then be reinserted into the sheath. In addition, as mentioned above, the disclosed technique can be used in other medical devices which are not implanted but are placed on the body of a patient and have a string-like shape. This may include stimulation devices which include replaceable sticky patches that are placed on the body. Besides holding the device, these patches provide electrical impulses to the patient and can be coupled via a device having a string-like shape, which includes a power source and necessary electronics for providing the electrical impulses to the patches. The power source itself may be embodied as a single battery, a plurality of batteries or a plurality of batteries using hybrid battery chemistry.

As mentioned above, many implantable medical devices require a power source for delivering electrical pulses to various parts of the body. Such electrical pulses can be used to regulate various organs and systems of the body. Prior art implantable medical devices usually separate the power source from the electrodes which actually deliver the electrical pulses to at least one location in the body, thus resulting in an implantable medical device having at least two parts placed in different positions within a patient. The disclosed technique provides for a battery configuration enabling the power source to be integrated into the same housing as the electrodes, thus forming an implantable medical device having only one part and being essentially unitary. In general, the disclosed technique relates to any implantable medical device having a flexible string shape. Examples of such string shapes are shown below in FIGS. 5, 6, 7 and 8. In addition, other examples of such a device can be found in U.S. Provisional Patent Application No. 61/728,897 and U.S. Provisional Patent Application No. 61/765,195, both to the same inventors of the current patent application. These patent applications relate to a pacemaker and defibrillator having a string shape which can be implanted in a patient subcutaneously. Other types of implantable medical devices having a string shape include a string-shaped pacemaker, a string-shaped defibrillator or ICD (implantable cardioverter defibrillator), a string-shaped heart device combining pacing and defibrillation functions (i.e., a device similar to prior art implanted cardiac resynchronization devices (CRT-Ds) except in the shape of a string and not having a separate can and leads design), a string-shaped spine stimulator, a string-shaped neurostimulation device for pain management, a string-shaped brain stimulator for deep brain stimulation and for aiding patients with sleep apnea, a string-shaped brain pacemaker and the like. The disclosed technique can also be used for medical devices having the above mentioned string shape, such as implantable pain control devices, implantable bladder stimulator devices, implantable sphincter control devices, implantable neurostimulator devices, implantable drug delivery devices and implantable monitoring devices.

In general, the terms "string shape," "flexible string shape" and "string-like shape" as used herein with reference to a medical device refer to any type of medical device having the following characteristics:

- can provide any known stimulation type therapy, wherein an organ, a muscle or a part thereof, is stimulated via electrical impulses;
- is embodied as a single unit, including the power source, electrodes and any other electronics (such as a CPU, at least one capacitor and the like) required to provide the electrical impulses as stimulation (thus not having a separate can and leads configuration as described in the prior art);
- can be positioned inside a patient endovascularly, subcutaneously, internally, percutaneously and the like, yet can also be positioned externally to (i.e., on the outer surface of) the patient's body;
- can be positioned inside a semi-rigid sheath such that it can be easily inserted and removed from the sheath, even if the sheath is implanted inside a patient (i.e., sheath remains implanted while ICD is removable with respect to the position of the sheath);
- has a generally tubular or cylindrical shape with a cross-sectional shape having any known curvature. For example, the cross-sectional shape may be a circle, an ellipse, a polygon, a closed curve and the like. The cross-sectional shape may also be any conic section having an eccentricity ranging from 0 to 1. In addition, the cross-sectional shape may vary or change over length, being different at a distal end as compared to a proximal end of a medical device.

An implantable medical device having a string shape according to the disclosed technique integrates the full functionality of a medical device used for stimulating internal organs, via the administration of electrical pulses, into a single flexible structure having the shape of a flexible string. Such a structure will include at least one sensing electrode, for acquiring and measuring a biological signal from an organ of interest (such as the heart, the brain, the lungs and the like), at least one signal delivery electrode, for delivering an electrical pulse as a way to synchronize the organ of interest or provide a therapy to it, a processor, for analyzing the acquired and measured biological signal and determining what type of electrical signal should be administered to the organ of interest (for example, the strength of the electrical pulse, the frequency or rate at which the electrical pulse should be delivered, the total amount of time the electrical pulse should be delivered and the like) and a power source, such as a battery, for providing the implantable medical device with a substantially continuous supply of power. In some structures, a capacitor and an electronic circuit may also be included in order to generate and store a high voltage for generating a high current electric shock, as is needed in the case of defibrillation. It is noted that the capacitor and electronic circuit may be embodied as a plurality of capacitors coupled together via coils, resistors, transistors, diodes and/or other appropriate electronic components depending on the voltage, energy and waveform required. The coupling of the capacitors can also be either in series, parallel or a mixture of the two. This is a matter of design choice depending on which internal organ or organs are to be stimulated and what kind of stimulation therapy is to be applied to the organ or organs. In such structures the power source is also used in the building up of such a high voltage electrical pulse. Such a structure is novel in that all the components of the implantable medical device are integrated into a single structure or a core structure. This is unlike prior art implantable medical devices which include a can and a pair of leads, where the can is used to house the processor, the power source and the capacitor (if required) while the pair of leads house both the sensing and signal delivery electrodes. In such prior art devices, the pair of leads are coupled with the can, and particularly with the internal components housed in the can. As mentioned above, the power source may be embodied as a single battery, a plurality of batteries or a plurality of batteries using hybrid battery technology.

In general, the power source in implantable medical devices requires the most amount of volume relative to the volume occupied by other components and according to the prior art thus requires a separate can in which it is housed. According to the disclosed technique, the power source of an implantable medical device is integrated into the same housing which includes the sensing and signal delivery electrodes along with the processor, and if required, the capacitor as well, thus forming a core structure. As mentioned above, the capacitor may be embodied as a plurality of capacitors coupled together with coils and other appropriate electronic components in series, in parallel or in both. As described, the plurality of capacitors and electronic components, according to the disclosed technique form part of the core structure. Thus the disclosed technique eliminates the need for an implantable medical device to have a can and leads design, wherein the can may be implanted in one part of a patient, with the leads implanted in another part of the patient and the two elements (can and leads) are coupled together into a single solitary device. It is noted that in another embodiment of the disclosed technique, a plurality of string-shaped implantable medical devices can be coupled together (for example, in series), thus forming a multiple string-shaped implantable medical device. Such a device might be used when the implantable medical device is to serve multiple functions, such as acting as a pacemaker as well as a defibrillator. In such a case, the various functions may be split amongst the implantable medical devices. For example, a first string-shaped implantable medical device might include electronics for enabling the pacing function whereas a second string-shaped implantable medical device might include electronics for enabling the defibrillation function. Both string-shaped implantable medical devices are coupled together, however, and thus function together as one implantable medical device. In another embodiment, the electronics for both the first string-shaped implantable medical device and the second string-shaped implantable medical device may be inserted in only one of the string-shaped implantable medical devices. Thus, the two implantable medical devices each serve a different function (one for the pacing function and another for the defibrillation function) yet the electronics are placed in only one of the implantable medical devices.

Figure 2:
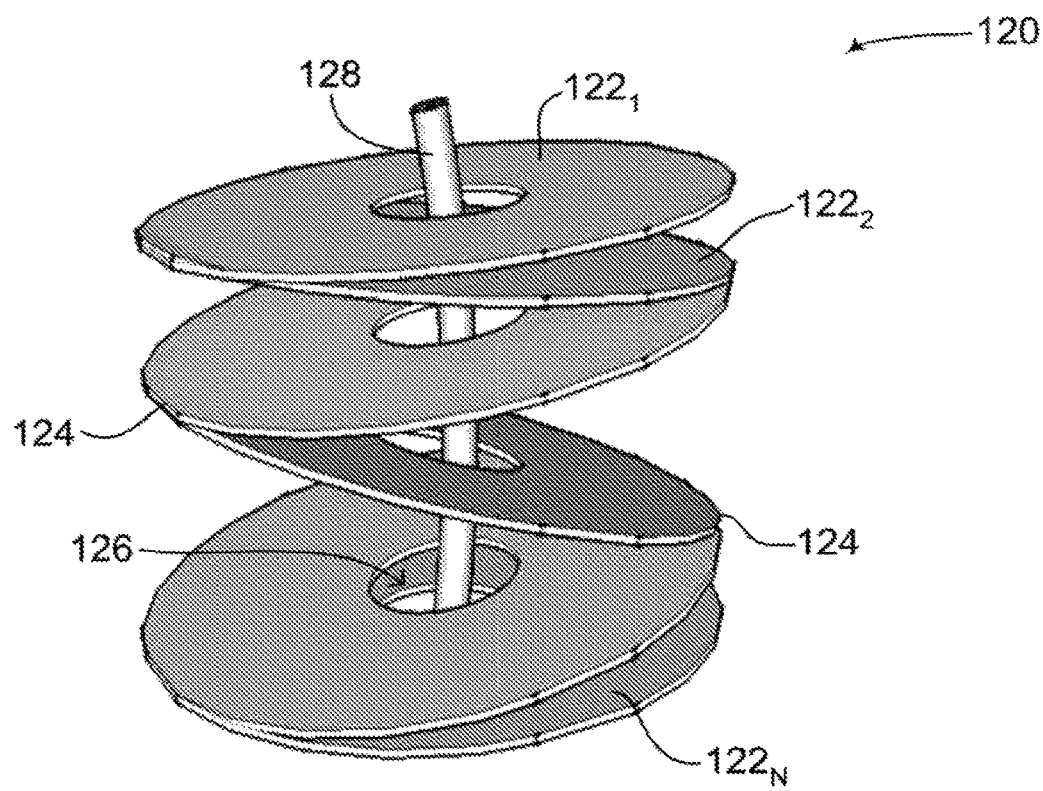
FIG. 2 is a schematic illustration of a second battery configuration, constructed and operative in accordance with another embodiment of the disclosed technique.

Reference is now made to FIG. 1, which is a schematic illustration of a first battery configuration, generally referenced 100, constructed and operative in accordance with an embodiment of the disclosed technique. Battery configuration 100 shows how a battery can be designed such that it can be incorporated in a string-shaped implantable medical device while enabling the medical device to have a significant amount of flexibility. For example, battery configuration 100 can be achieved using thin film battery technology, and more specifically FIG. 1 shows how three dimensional (herein abbreviated 3D) thin film battery technology, which can be configured to have a long and narrow flexible shape, as shown in FIG. 1, can be integrated into a string-shaped implantable medical device. 3D thin film batteries are known in the art, examples of which are disclosed in the following prior art documents: U.S. Pat. Nos. 6,197,450, 7,527,897, 7,618,748 and U.S. Patent Application Publication No. 2006/0032046. In addition, other micro-sized energy storage cells can be used to create the battery configuration as shown in FIG. 1. For example, Reissued U.S. Pat. Nos. RE41,578 and RE42,273 describe thin film micro-electrochemical energy storage cells which can be formed and coupled as shown in FIGS. 1 and 2 such that they can be incorporated into a string-shaped implantable medical device. As shown below, any known thin film battery can be used and configured according to the disclosed technique. For example, two dimensional (herein abbreviated 2D) battery technology can be used to construct the battery configuration shown in FIGS. 1 and 2.

Battery configuration 100 includes a plurality of thin film batteries $102_1$, $102_2$ and $102_N$. Each thin film battery is a battery onto itself, yet can be coupled with another thin film battery via a pair of connectors (not shown), thus forming a continuous thin film battery of greater power. As shown in FIG. 1, each of plurality of thin film batteries $102_1$, $102_2$ and $102_N$ is coupled to its neighboring thin film battery at locations 104. The connectors (not shown) at locations 104 enable each one of plurality of thin film batteries $102_1$, $102_2$ and $102_N$ to rotate, at least partially, around an axis (not shown), similar to a hinge. Plurality of thin film batteries $102_1$, $102_2$ and $102_N$ thus forms an accordion-like shape. Similar to an accordion, plurality of thin film batteries $102_1$, $102_2$ and $102_N$ is thus flexible due to the ability of each thin film battery to rotate around the axes of locations 104. It is noted that each one of plurality of thin film batteries $102_1$, $102_2$ and $102_N$ may be a rigid surface, such as a silicon substrate, or may be fabricated from a flexible material. As rigid surfaces, plurality of thin film batteries $102_1$, $102_2$ and $102_N$ still provide flexibility to an implantable medical device they are integrated with, since each thin film battery can partially rotate around the axis at which it is coupled with an adjacent or neighboring thin film battery. The volume taken up by battery configuration 100 can be decreased by folding each one of plurality of thin film batteries $102_1$, $102_2$ and $102_N$ on top of one another completely (not shown). The plurality of thin film batteries thus forms one long continuous battery. It is also noted that battery configuration 100 can be formed from a single flexible thin film battery which is folded over multiple times in an accordion-like manner. In addition, it is also possible to rebuild used regular batteries into the battery configuration shown in FIG. 1, such that batteries not built from thin film technology can be used with the disclosed technique. Battery configuration 100 may also include hybrid battery chemistry in which a first portion of the thin film batteries are used for constant powering (e.g., in the case of sensing electrical activity of an organ) whereas a second portion of the thin film batteries are used for occasional powering (e.g., in the case of electric shock delivery) or for high current drain applications during limited periods.

Reference is now made to FIG. 2, which is a schematic illustration of a second battery configuration, generally referenced 120, constructed and operative in accordance with another embodiment of the disclosed technique. Battery configuration 120 is similar to battery configuration 100 (FIG. 1), including a plurality of thin film batteries $122_1$, $122_2$ and $122_N$ each coupled with its neighboring thin film battery at a location 124. As mentioned above, the plurality of batteries can be other types of batteries and not just those using thin film technology. The mention of thin film technology batteries herein is merely brought as an example of how to embody the disclosed technique. The disclosed technique however applies to any kind of battery which can be formed so as to give a string-shaped implantable medical device sufficient flexibility. However, in FIG. 2, each thin film battery has been reshaped as a disc. It is noted that according to the disclosed technique, the thin film batteries may be shaped into any desirable shape. The disc shape of the thin film batteries in flexible battery configuration 120 includes a central hole 126. Once each one of plurality of thin film batteries $122_1$, $122_2$ and $122_N$ is folded onto its neighbor, battery configuration 120 will have a cylindrical and flexible shape and can thus be inserted into a tubular or string-like structure, thus simplifying its insertion into and removal from medical devices having a string-like shape. In addition, due to central hole 126, a space or channel is created within battery configuration 120 wherein wires, cables and connections can be passed through. As shown below in FIGS. 3 and 6, when the battery configuration is integrated into a string-shaped implantable medical device, the channel of central hole 126 can be used to couple various parts and components of the device together. For example, as shown in FIG. 2, a wire 128 can be threaded through central hole 126. In addition, the channel of central hole 126 can be used to insert wires, guidewires and stylets through, for example when the device is being initially implanted in a patient (not shown). It is noted that central hole 126 does not need to necessarily be centered in each one of plurality of thin film batteries $122_1$, $122_2$ and $122_N$. The disc shape of plurality of thin film batteries $122_1$, $122_2$ and $122_N$ can be formed such that a hole of any shape, size and location is possible. The hole (not shown) may be, for example, square or triangular in shape. The hole (not shown) may be off-centered or located at one of the edges of each thin film battery, as shown below in FIG. 3. Furthermore, the hole (not shown) may be larger or smaller in diameter than central hole 126.

Figure 3:
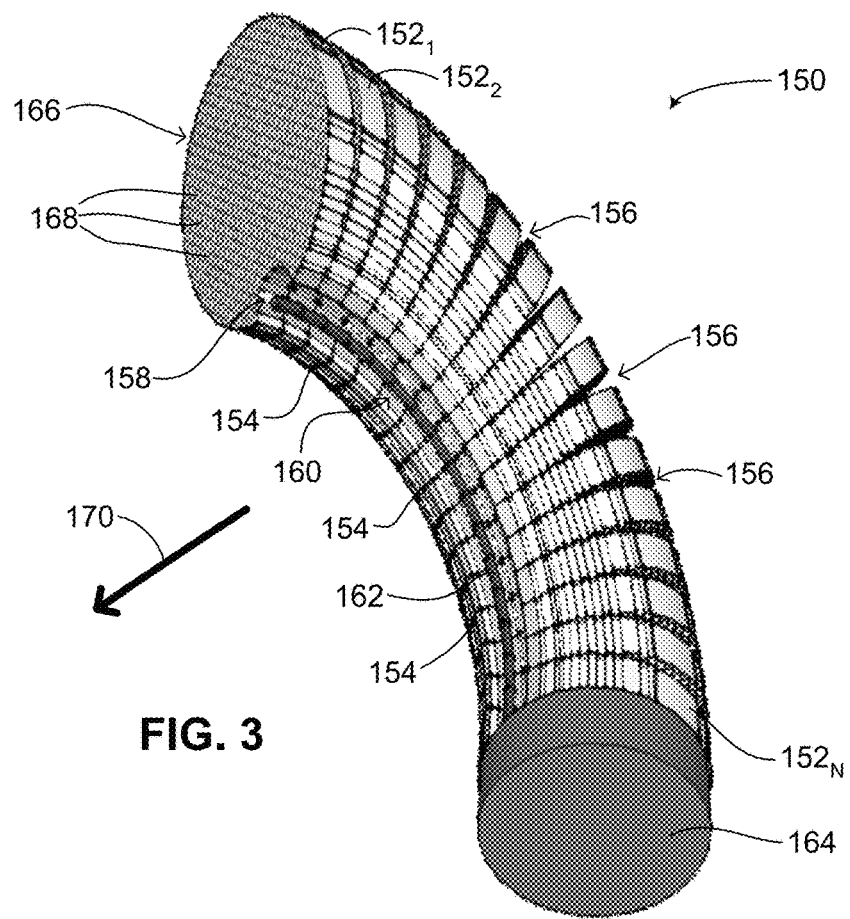
FIG. 3 is a schematic illustration of a third battery configuration, constructed and operative in accordance with a further embodiment of the disclosed technique.

Reference is now made to FIG. 3, which is a schematic illustration of a third battery configuration, generally referenced 150, constructed and operative in accordance with a further embodiment of the disclosed technique. Third battery configuration 150 is similar to second battery configuration 120 (FIG. 2) and includes a plurality of thin film batteries $152_1$, $152_2$ and $152_N$. As mentioned above, the batteries may also be fabricated using technologies other than thin film battery technology. However, in FIG. 3, as opposed to FIGS. 1 and 2, each thin film battery is coupled with its neighbor at points 154, where each point 154 is located on the same side of battery configuration 150. As such, battery configuration 150 can be bent in one general direction, shown by an arrow 170, thus giving battery configuration 150 a measurable amount of flexibility. As battery configuration 150 is bent in the direction of arrow 170, a plurality of spaces 156 forms between adjacent thin film batteries on the side opposite where each point 154 is located. As an example of one type of battery which can be used with the disclosed technique, a surface 166 of thin film battery $152_1$ is shown, showing a plurality of holes 168 which are each filled with an electrochemical substance for storing charge and electrical energy. Such a thin film battery (although not the battery configuration as shown in FIG. 3) is described in Reissued U.S. Pat. No. RE41,578, as mentioned above.

In addition, unlike the battery configuration of FIG. 2, each one of plurality of thin film batteries $152_1$, $152_2$ and $152_N$ is formed in the shape of a circle, with a small circular portion 158 cut out on the side where each point 154 is located. Thus, similar to central hole 126 (FIG. 2), a channel 160 is formed by each small circular portion 158 such that a wire 162 can pass there through. As mentioned above, the formed channel does not need to be centrally located on each thin film battery. According to the disclosed technique, channel 160 can be formed anywhere on the surface of the thin film batteries, and not just in the center or on the edge of the thin film batteries; thus the examples of a channel as shown in FIGS. 2 and 3 are merely brought as examples. In addition, the battery configuration of the disclosed technique may include a plurality of channels formed within the thin film batteries, for example a central channel (not shown) and channel 160. As shown as well in FIG. 3, an end of battery configuration 150 includes an electronics unit 164, which is coupled with wire 162. Electronics unit 164 may include a processor (not shown), at least one capacitor and other electronics necessary for the functioning of the implantable medical device battery configuration 150 is inserted into.

Figure 4:
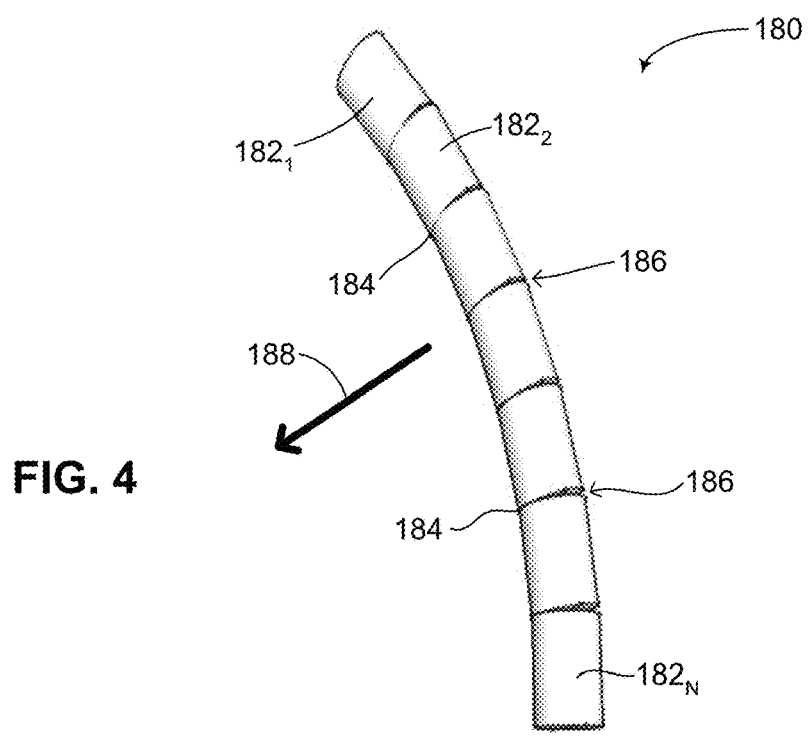
FIG. 4 is a schematic illustration of a fourth battery configuration, constructed and operative in accordance with another embodiment of the disclosed technique.

Reference is now made to FIG. 4, which is a schematic illustration of a fourth battery configuration, generally referenced 180, constructed and operative in accordance with another embodiment of the disclosed technique. Fourth battery configuration 180 is similar to the other battery configurations disclosed thus far, however, fourth battery configuration 180 includes a plurality of segments $182_1$, $182_2$ and $182_N$. Each one of plurality of segments $182_1$, $182_2$ and $182_N$ includes a plurality of thin film batteries. Thus segment $182_1$ includes a plurality of thin film batteries (not shown), segment $182_2$ also includes a plurality of thin film batteries (not shown) and segment $182_N$ further includes a plurality of thin film batteries (not shown). Alternatively, each one of plurality of segments $182_1$, $182_2$ and $182_N$ may include a single rigid battery. The thin film batteries in each segment are rigidly coupled with one another. As shown, each segment is coupled to an adjacent segment at points 184. Similar to FIG. 3, segments are coupled together on the same side, thus forming spaces 186 when battery configuration 180 is bent in the direction of an arrow 188. Battery configuration 180 is actually semi-flexible in nature as compared to the battery configurations in FIGS. 2 and 3, since each segment includes a plurality of thin film batteries which are rigidly coupled with one another. Nonetheless, battery configuration 180 is flexible due to the segmentation of its parts (i.e., plurality of segments $182_1$, $182_2$ and $182_N$) and enables easy insertion into and removal from a string-like medical device, whether implantable or non-implantable. Due to the constraints of a string-like medical device, especially one which is implantable, each one of plurality of segments $182_1$, $182_2$ and $182_N$ should be smaller than 11 millimeters in diameter and shorter than 5 centimeters in length.

Figure 5:
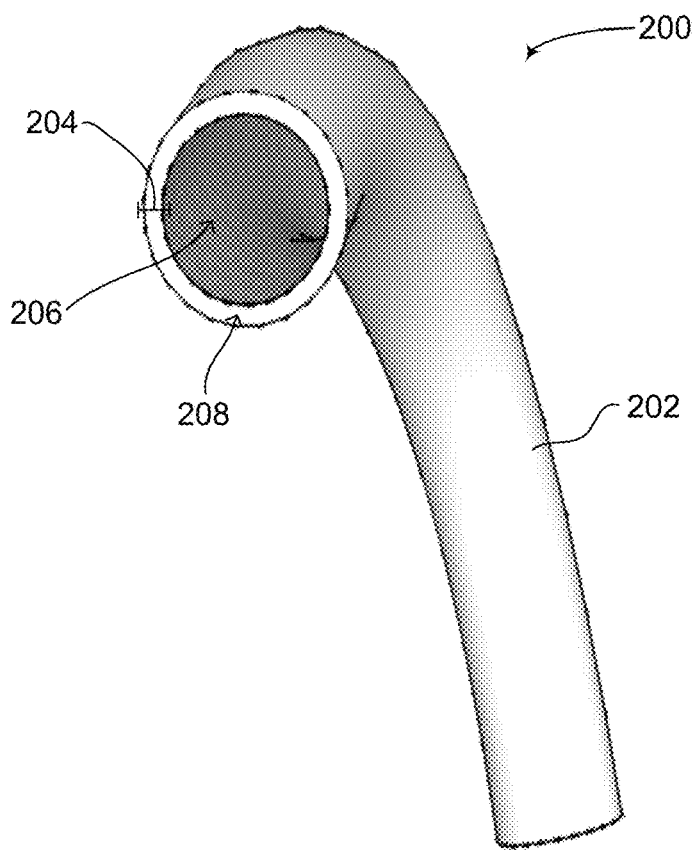
FIG. 5 is a schematic illustration of an implantable medical device having a flexible string shape, constructed and operative in accordance with a further embodiment of the disclosed technique.

Reference is now made to FIG. 5, which is a schematic illustration of an implantable medical device having a flexible string shape, generally referenced 200, constructed and operative in accordance with a further embodiment of the disclosed technique. Implantable medical device 200 includes a sheath 202, having a thickness 204 and a hollow space 206. Implantable medical device 200 is designed to house various elements such as a sensing electrode (not shown), a signal delivery electrode (not shown) and possibly also electronics (not shown) along sheath 202 as shown by an arrow 208. Such an implantable medical is described in U.S. Provisional Patent Application No. 61/728,897 and U.S. Provisional Patent Application No. 61/765,195, as mentioned above. As described below, hollow space 206 can be used to house a battery having one of the battery configuration described above in FIGS. 1-4. Hollow space 206 substantially houses a core, which includes one of the battery configurations described above along with addition electronics required for providing electrical impulses and stimulation therapies. It is noted that the battery configurations described above may employ hybrid battery chemistry in which the components comprising the battery configuration are sub-divided into a plurality of groups or portions. For example, a first portion of the components comprising the battery configuration might be used to constantly power parts of implantable medical device 200 which require a constant source of power, such as a processor and electronics (both not shown) for recording the sensed electrical activity of an internal organ and determining what kind of electrical impulse should be delivered to the internal organ. A second portion of the components comprising the battery configuration might be used to occasionally power parts of implantable medical device 200 which are only used in certain circumstances. For example, if implantable medical device 200 includes at least one capacitor for storing the energy required for generating a high voltage shock and voltage amplification electronics, then the aforementioned second portion may be used for powering the amplification electronics used for building up voltage on the at least one capacitor. In general, one of the main type of therapies that a medical device, such as an ICD, can deliver is the application of electric shocks to organs or tissues in the body. At least one capacitor is used to store electrical energy required for generating a high voltage. An electric shock to be delivered as the therapy is the discharging of the stored electrical energy through the organs or tissues of a patient. Since high voltage shocks are not administered constantly but only under certain circumstances, the life of a battery having one of the configurations mentioned above can be extended by dedicating a portion of the battery to being constantly used whereas another portion of the battery is used only when needed. In another embodiment, a portion of the battery is used for high current intermittent applications whereas the other portion is used for lower current continuous applications. Hybrid chemistry to support these dual functions can also be incorporated into such a battery.

Figure 6:
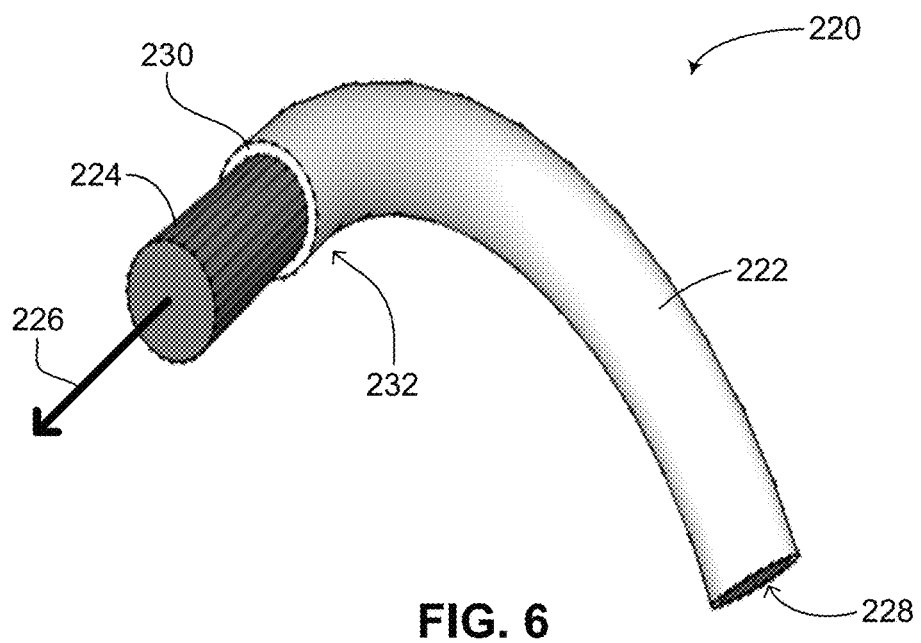
FIG. 6 is a schematic illustration of a battery integrated into the implantable medical device of FIG. 5, constructed and operative in accordance with another embodiment of the disclosed technique.

Reference is now made to FIG. 6, which is a schematic illustration of a battery integrated into the implantable medical device of FIG. 5, generally referenced 220, constructed and operative in accordance with another embodiment of the disclosed technique. As shown, an implantable medical device 222 includes a sheath 230 and a hollow space 228. A battery 224 is positioned in hollow space 228 in sheath 230. Battery 224 has a configuration according to the disclosed technique, such as those described above in FIGS. 1-4 and can be referred to as a core structure. Also as shown, implantable medical device 222 has a flexible string shape. FIG. 6 shows how according to the disclosed technique, battery 224 can be replaced easily and simply without having to remove implantable medical device 222 from a patient (not shown), thus not requiring any major surgery to replace battery 224. Implantable medical device 222 is positioned subcutaneously in a patient. It is noted that implantable medical device 222 may also be positioned in a patient such that a first part of the device is positioned subcutaneously whereas a second part of the device is positioned internally, such as under the ribs. Implantable medical device 222 may include a cover (not shown) at each end for enclosing battery 224 within hollow space 228. The cover may also serve the purpose of electrically coupling battery 224 to any electronics (not shown) housed in sheath 230, such as found in certain handheld flashlight designs. As mentioned in FIG. 5, sheath 230 may house various electrodes (not shown) as well as other elements of the implantable medical device (excluding the battery) which do not typically require replacement over time, such as electronics and capacitors (not shown). As mentioned above, battery 224 is electrically coupled (not shown) with sheath 230 and any electronics housed therein. According to another embodiment of the disclosed technique, such as the battery configuration shown above in FIG. 3, any electronics and capacitors may be coupled with battery 224 and configured to also fit within hollow space 228. In such an embodiment, battery 224 is coupled with sheath 230 such that the electrodes in sheath 230 are coupled with the electronics coupled with battery 224. In a further embodiment, battery 224 may be constructed to include electronics (not shown) and at least one capacitor (not shown), thus also forming a core structure. In all embodiments, the cover is designed to securely keep battery 224, the core structure, coupled with sheath 230 such that battery 224 is not unintentionally disconnected from sheath 230.

Once battery 224 is out of power and needs to be replaced, battery 224 can be easily pulled out of sheath 230, as shown by an arrow 226, through a small incision (not shown) made in the skin of a patient just above the position of the cover. Once the old battery is pulled out, a new battery or core structure (not shown) can then be inserted into hollow space 228 through the incision. The incision can then be easily sewed up. Thus sheath 230 can be left in a patient and does not need to be removed in order to replace the battery of the implantable medical device. The replacement of battery 224 can thus be performed easily and quickly without causing any unnecessary pain or discomfort to the patient. When implantable medical device 222 is implanted subcutaneously, battery 224 can be easily replaced via a minor surgical procedure. A small incision is made in the area where a proximal end 232 of implantable medical device 222 is located. Proximal end 232 is then exposed and a cover (not shown) covering proximal end 232 is opened and temporarily removed. Battery 224 inside sheath 230 is pulled out and a new fresh battery (not shown) is inserted. The new battery may need to be coupled electrically with sheath 230 or may be coupled electrically once the cover is put back. The cover is then put back on proximal end 232 and the small incision is sutured. As described, battery 224 (which is a core structure) can be replaced without having to remove sheath 230 from the patient, thereby greatly simplifying the procedure by which the power source of an implantable medical device is replaced. Such a procedure is fast and easy and does not require any major surgery. In general, since implantable medical device 222 will have been inside a patient for quite a bit of time before battery 224 needs to be replaced, during that time sheath 230 will have become coupled with the tissue surrounding it, therefore as battery 224 is removed, sheath 230 will remain in place. Thus battery 224 can be replaced without having to remove sheath 230 from the patient. It is noted as well that implantable medical device 222 has a rigid outer shape (i.e., sheath 230), such that when battery 224 is removed, sheath 230 retains its shape so that a new battery can be inserted into hollow space 228 without too much difficulty. As described below in FIG. 7, the sheath surrounding the battery may also surround the electronic components of the implantable medical device. In such an embodiment (not shown in FIG. 6), the sheath enables the electronic components, which may be formed in a string-like shape, to be easily removed and inserted. Therefore, just as battery 224 can be easily removed and reinserted into sheath 230, the electronic components can also be easily removed and reinserted into sheath 230.

Figure 7:
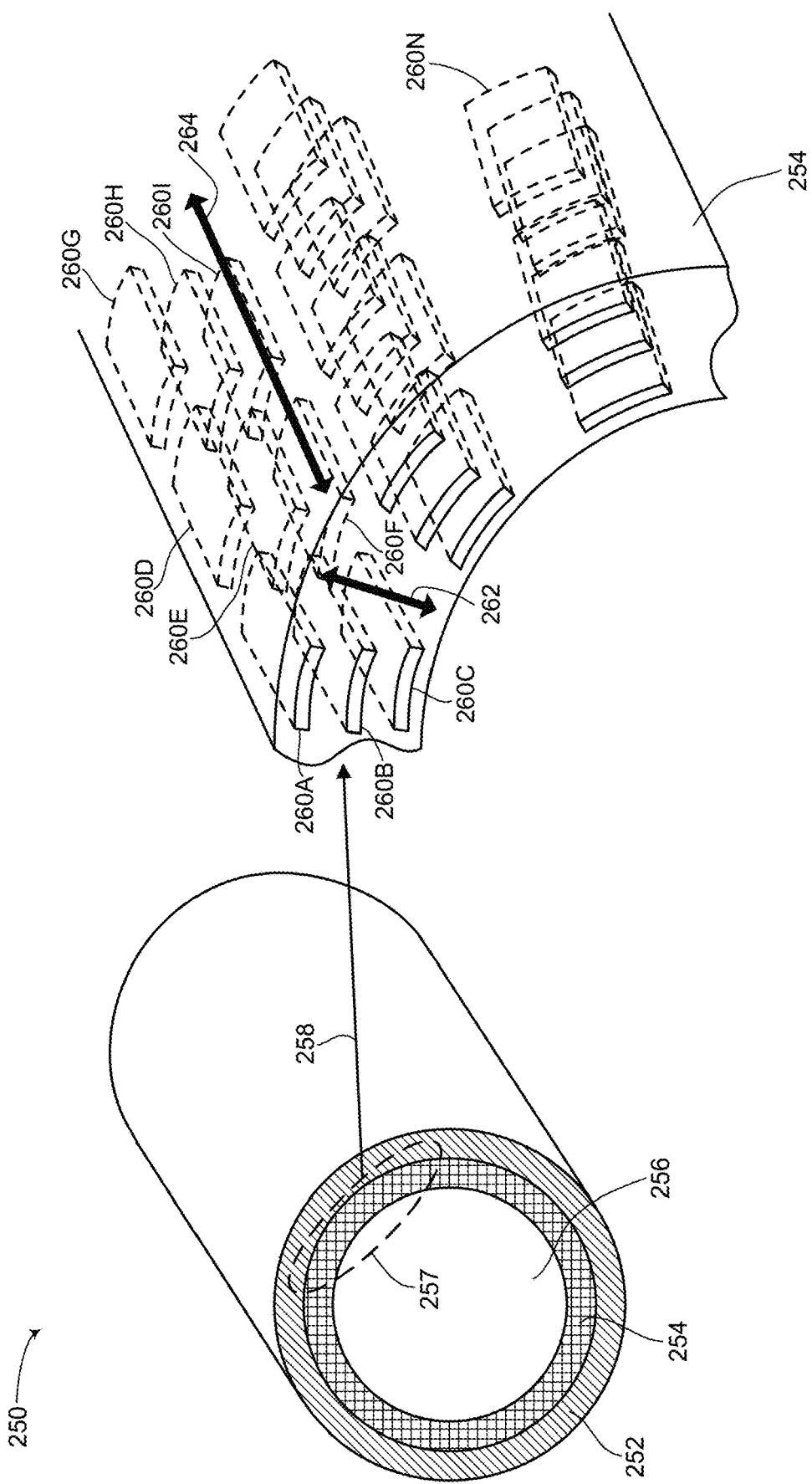
FIG. 7 is a schematic illustration and close-up of an implantable medical device with a removable battery, constructed and operative in accordance with a further embodiment of the disclosed technique.

Reference is now made to FIG. 7, which is a schematic illustration and close-up of an implantable medical device with a removable battery, generally referenced 250, constructed and operative in accordance with a further embodiment of the disclosed technique. Implantable medical device 250 includes an outer sheath 252, a battery 254 and a main unit 256. Outer sheath 252, battery 254 and main unit 256 each have a generally circular cross-sectional shape, thus enabling main unit 256 to be inserted into battery 254 and battery 254 to be inserted into outer sheath 252. Each one of outer sheath 252, battery 254 and main unit 256 has a flexible shape. Outer sheath 252 may be constructed from a semi-rigid material, thus enabling battery 254 and main unit 256 to be removed from outer sheath 252 with outer sheath 252 maintaining its shape. Battery 254 and main unit 256 are both core structures which can be easily removed and inserted into outer sheath 252. In general, battery 254 and main unit 256 can be constructed as a single core structure or as two separate core structures. In this manner, with implantable medical device 250 implanted subcutaneously in a patient, battery 254 and main unit 256 can be simply removed from outer sheath 252 while leaving outer sheath 252 still inside the patient. According to the disclosed technique, a new battery, a new main unit or both can then be easily reinserted into outer sheath 252.

Main unit 256 may include all the elements and components needed for implantable medical device 250 to function minus its power source. For example, main unit 256 may include electrical leads (not shown), capacitors (not shown), a processor (not shown) and other necessary electronics for providing electrical impulses to the patient. Power is provided to these elements and components from battery 254. As mentioned above, battery 254 may include hybrid battery chemistry, where a portion of battery 254 is used to constantly power elements like a processor or provide electrical impulses to electrical leads and another portion of battery 254 may be used to occasionally load the capacitors when needed. In one embodiment, as shown, main unit 256 and battery 254 are two separate entities which are coupled together. In another embodiment (not shown), main unit 256 and battery 254 are constructed as a single entity. A section 257 of implantable medical device 250 is shown in a close-up, as indicated by an arrow 258. The close-up is of battery 254 and how it is constructed.

Battery 254 has a generally circular cross-sectional shape, having a particular thickness, as shown by an arrow 262 and a particular length, as shown by an arrow 264. Battery 254 includes a plurality of small 3D thin film batteries 260A, 260B, 260C, 260D, 260E, 260F, 260G, 260H, 260I and 260N. The plurality of 3D thin film batteries can be arranged in rows and columns along the length and thickness of battery 254. As shown in FIG. 7, 3D thin film batteries 260A, 260B and 260C are arranged in a column and 3D thin film batteries 260A, 260D and 260G are arranged in a row. The plurality of 3D thin films batteries shown is merely schematic. Battery 254 may include thousands of small 3D thin film batteries arranged in a compact configuration within the thickness of battery 254. Each one of 3D thin film batteries 260A-260N may be flexible or rigid. In either case, their configuration within the thickness of battery 254 provides battery 254 with a degree of flexibility. As shown in FIG. 7, battery 254 substantially represents a plurality of layers of small 3D thin film batteries surrounding and encompassing main unit 256. Battery 254 is coupled with main unit 256 such that battery 254 can provide power to the various components of main unit 256. Various methods of coupling a battery to components which require power are known in the art. The type of coupling of battery 254 to main unit 256 is thus a matter of design choice and is known to the worker skilled in the art.

Figure 8:
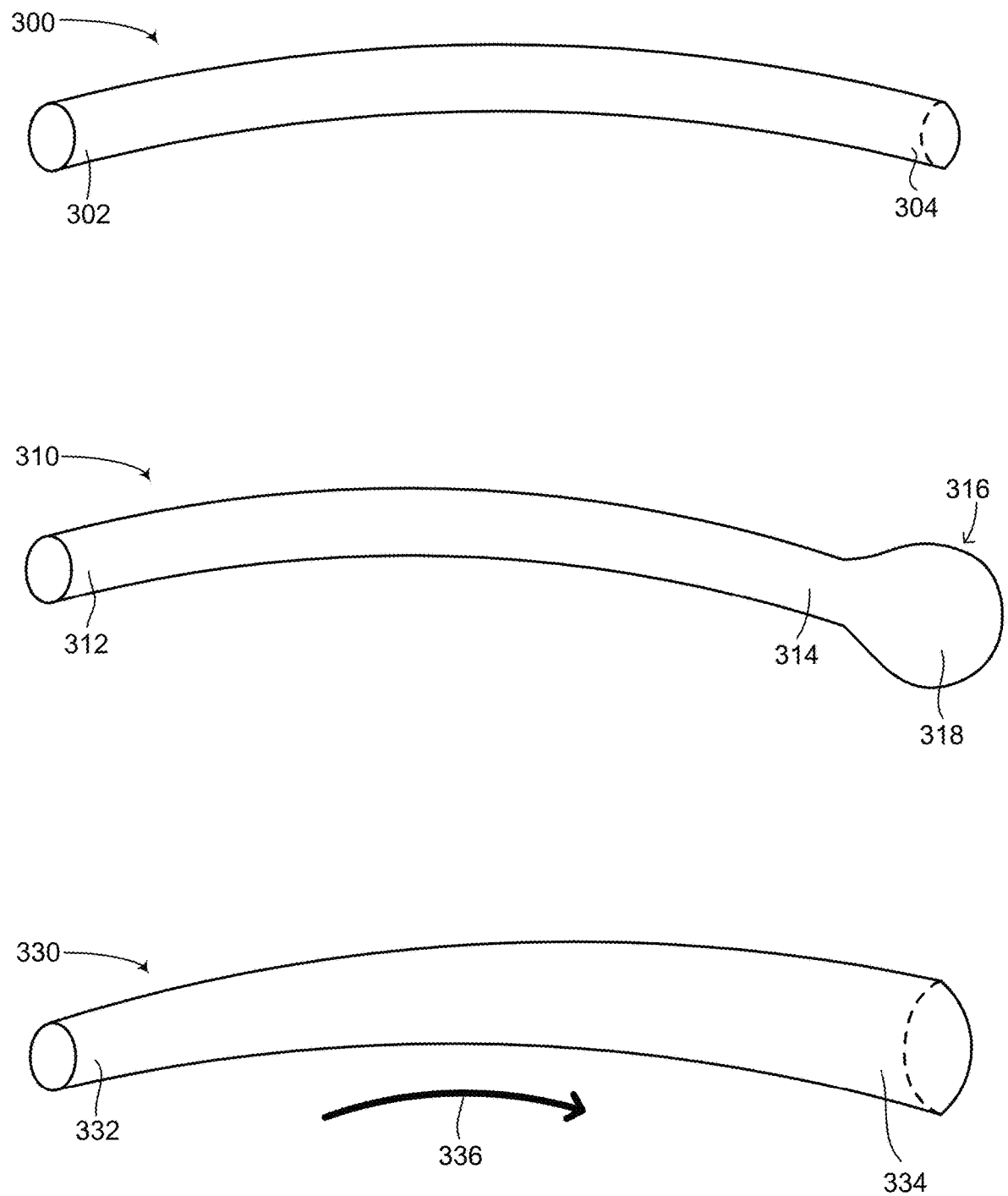
FIG. 8 is a schematic illustration of various possible shapes for an implantable medical device having a flexible string shape, constructed and operative in accordance with another embodiment of the disclosed technique.

Reference is now made to FIG. 8 which is a schematic illustration of various possible shapes for an implantable medical device having a flexible string shape, generally referenced 300, 310 and 330 respectively, constructed and operative in accordance with another embodiment of the disclosed technique. Flexible string shapes 300, 310 and 330 may be the shape of a core structure including a battery and other electronics, such as battery 254 (FIG. 7), main unit 256 (FIG. 7) or both, as described above. Flexible string shapes 300, 310 and 330 may also be the shape of a sheath into which a core structure including a battery and other electronics may in inserted into, such as outer sheath 252 (FIG. 7), as described above. In general, each of the flexible string shapes described below is described as having a proximal end and a distal end. These labels however are merely for the purposes of describing the shapes and can easily be switched, such that the proximal end is referred to as the distal end and the distal end is referred to as the proximal end. Flexible string shape 300 includes a proximal end 302 and a distal end 304. Flexible string shape 300 has a generally cylindrical or tubular shape, characterized by a generally uniform cross-sectional shape and diameter along its length. Flexible string shape 310 includes a proximal end 312 and a distal end 316. Distal end 316 includes two sections, a bulbous end section 318 and an adjacent end structure 314. From proximal end 312 to adjacent end structure 314, flexible string shape 310 substantially resembles flexible string shape 300, having a generally cylindrical or tubular shape, characterized by a generally uniform cross-sectional shape and diameter along its length. However, distal end 316 has bulbous end section 318 which is larger in diameter than adjacent end structure 314. Bulbous end section 318 has a generally spherical or ellipsoidal shape, giving flexible string shape 310 on the whole a shape which resembles a tadpole. Flexible string shape 310 is one continuous shape, having bulbous end section 318 at its distal end. Bulbous end section 318 can be used to house a component of a medical device which cannot fit inside the section of flexible string shape 310 from proximal end 312 to adjacent end structure 314. For example, if at least one capacitor (not shown) is to be included in a medical device embodied as having a string shape, and the at least one capacitor is too large to be encapsulated along the length of the flexible string shape in its diameter then the at least one capacitor may be placed in bulbous end section 318. Additional electronic components may also be placed in bulbous end section 318 for coupling a plurality of capacitors together in order to generate a desired high voltage and specific waveform for a given stimulation therapy to be administered by the medical device, whether implantable or not. It is noted that if flexible string shape 310 is embodied as an implantable medical device then when implanted in a patient, proximal end 312 may be the distal end first inserted into the patient and distal end 316 may be the proximal end located near an incision made into the patient to insert the implantable medical device. Flexible string shape 330 includes a proximal end 332 and a distal end 334. Unlike flexible string shapes 300 and 310, flexible string shape 330 has a generally truncated conoid shape along its length. As shown in FIG. 8, in the direction of an arrow 336, the cross-section of the generally tubular or cylindrical shape of flexible string shape 330 changes over length, with the diameter of a cross-section of proximal end 332 increasing in the direction of distal end 334. Similar to flexible string shape 310, the increase in diameter over length of flexible string shape 330 enables larger components to be inserted into a medical device having such a shape. Therefore, a capacitor or other large electronic component (both not shown) which would not fit in proximal end 332 may be inserted in distal end 334 which has a larger diameter in its cross-section.

Figure 9A:
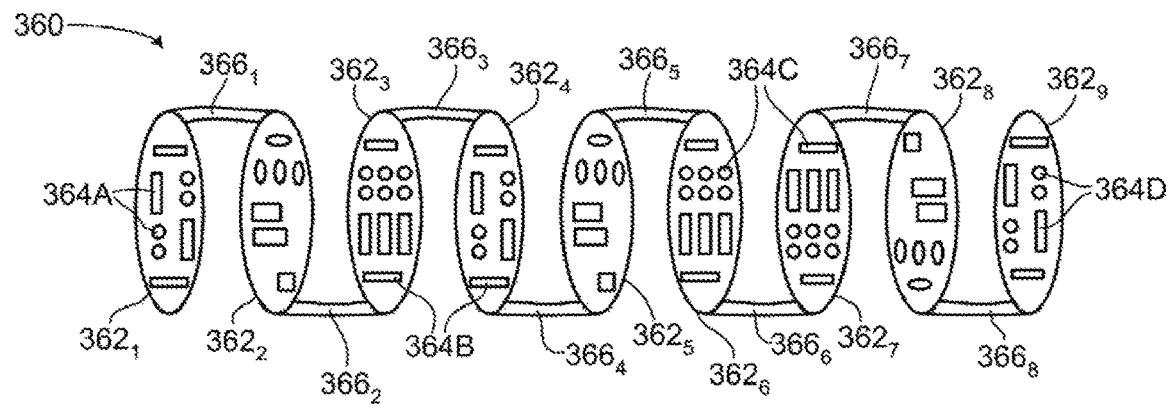
FIG. 9A is a schematic illustration of an encapsulation configuration for electronic components in a flexible implantable medical device, shown in an unfolded view, constructed and operative in accordance with a further embodiment of the disclosed technique.

In a similar manner to third battery configuration 150 (FIG. 3), electronic components to be used in a flexible medical device can be shaped and configured to fold in a cylindrical manner such that they can be encapsulated in a string-like or snake shaped medical device, whether implanted or not. Various embodiments for configuring electronic components in such a structure are described below in FIGS. 9A-10F. Reference is now made to FIG. 9A, which is a schematic illustration of an encapsulation configuration for electronic components in a flexible implantable medical device, shown in an unfolded view, generally referenced 360, constructed and operative in accordance with a further embodiment of the disclosed technique. Folding the electronic components in such manner enables them to later on be encapsulated into a cylindrical shape envelope or encasing and to become a part of a flexible string shape or snake-like shape medical device. As shown in FIG. 9A, electronic components in a medical device can be placed and divided up amongst a plurality of cylindrically or circularly shaped circuit boards (herein referred to as CB) $362_1$-$362_9$. Each one of CBs $362_1$-$362_9$ includes a plurality of electronic components, such as capacitors, resistors, transistors, switches, processors, transformers, diodes, ASICs (application specific integrated circuit), FPGAs (field-programmable gate arrays) and the like. For example, CB $362_1$ includes plurality of electronic components 364A, CBs $362_3$ and $362_4$ include plurality of electronic components 364B, CBs $362_6$ and $362_7$ include plurality of electronic components 364C and CB $362_9$ includes plurality of electronic components 364D. Each one of CBs $362_1$-$362_9$ has a substantially similar cylindrical or circular shape such that each CB can be placed adjacent to a subsequent CB. CBs $362_1$-$362_9$ are electrically coupled sequentially using a plurality of flat connection cables $366_1$-$366_8$. Flat connection cable $366_1$ couples CB $362_1$ with CB $362_2$, flat connection cable $366_2$ couples CB $362_2$ with CB $362_3$, flat connection cable $366_3$ couples CB $362_3$ with CB $362_4$, flat connection cable $366_4$ couples CB $362_4$ with CB $362_5$, flat connection cable $366_5$ couples CB $362_5$ with CB $362_6$, flat connection cable $366_6$ couples CB $362_6$ with CB $362_7$, flat connection cable $366_7$ couples CB $362_7$ with CB $362_8$ and flat connection cable $366_8$ couples CB $362_8$ with CB $362_9$. As shown, plurality of flat connection cables $366_1$-$366_8$ electrically couple between CBs alternatively at opposite ends of each CB, such as either the top of a CB or the bottom of a CB. Plurality of flat connection cables $366_1$-$366_8$ are flexible and are long enough to enable a first CB to be folded directly over a subsequent CB. Plurality of flat connection cables $366_1$-$366_8$ can also be embodied as connection cables which are not flat. In addition, other methods for coupling adjacent CBs together can be used in the disclosed technique, such as via male-female connector pairs positioned on opposite sides of adjacent CBs. Flat connection cables $366_1$, $366_3$, $366_5$ and $366_7$ electrically couple CBs at the top (i.e., at one side) of a CB whereas flat connection cables $366_2$, $366_4$, $366_6$ and $366_8$ electrically couple CBs at the bottom (i.e., at an opposite side) of a CB. This alternative coupling, as shown below in FIGS. 10A and 10B, enables one CB to be folded on top of another CB in a pleated manner, thereby forming a cylindrically shaped electronics configuration which can be encapsulated in a cylindrical enclosure.

Figure 9B:
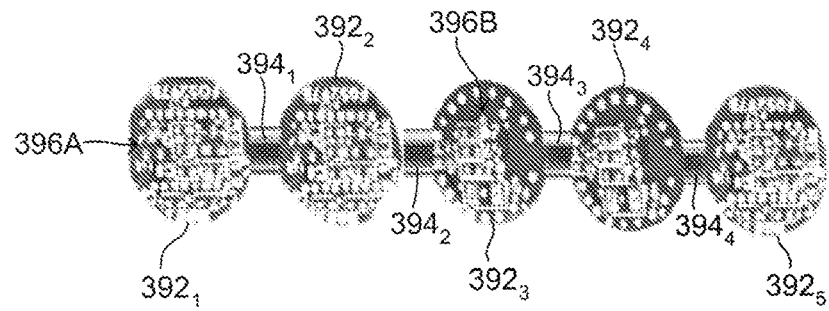
FIG. 9B is an image of electronic components in the encapsulation configuration of FIG. 9A, constructed and operative in accordance with another embodiment of the disclosed technique.

Reference is now made to FIG. 9B, which is an image of electronic components in the encapsulation configuration of FIG. 9A, generally referenced 390, constructed and operative in accordance with another embodiment of the disclosed technique. Shown in FIG. 9B is a plurality of CBs $392_1$-$392_5$ shaped in a circular fashion, electrically coupled sequentially by a plurality of flat connection cables $394_1$-$394_4$. Plurality of flat connection cables $394_1$-$394_4$ are each flexible and long enough to enable one CB to be folded onto its neighboring CB. Each CB includes a plurality of electronic components, such as electronic components 396A on CB $392_1$ and electronic components 396B on CB $392_3$. Plurality of CBs $392_1$-$392_5$ can be folded one on top of the other in a pleated or accordion-like manner, thereby forming a compact cylinder. As is understood by the worker skilled in the art, once folded, plurality of flat connection cables $394_1$-$394_4$ indeed coupled sequential CBs alternatively at their tops and bottoms.

Figure 10A:
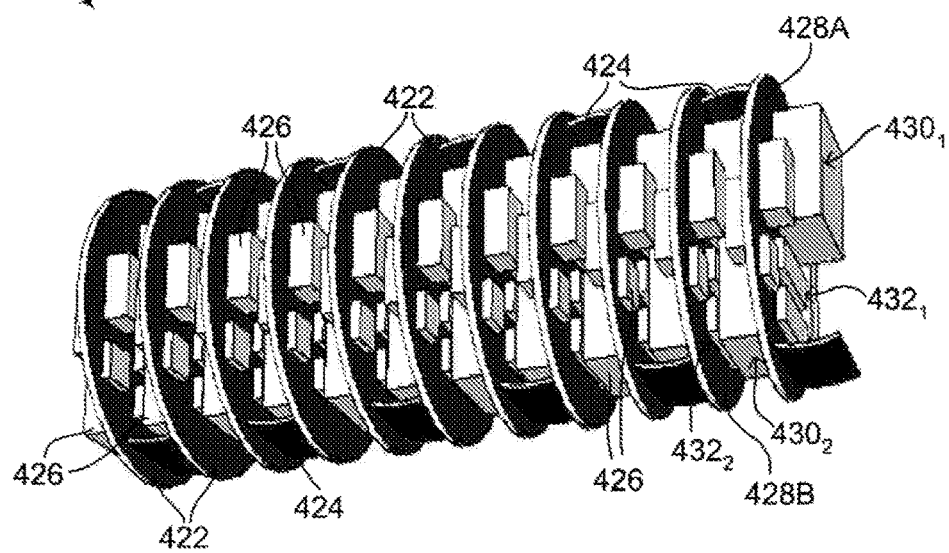
FIGS. 10A and 10B are schematic illustrations of the encapsulation configuration of FIGS. 9A and 9B shown in a folded view, constructed and operative in accordance with a further embodiment of the disclosed technique.
Figure 10B:
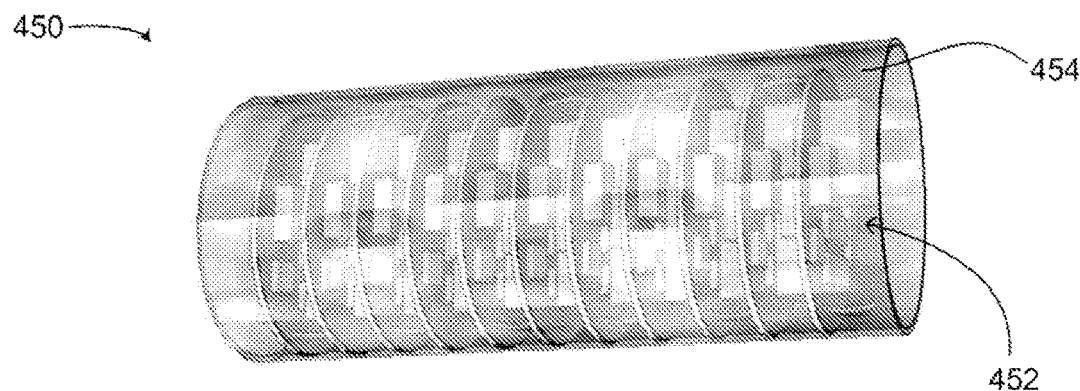

Reference is now made to FIGS. 10A and 10B, which are schematic illustrations of the encapsulation configuration of FIGS. 9A and 9B shown in a folded view, generally referenced 420 and 450 respectively, constructed and operative in accordance with a further embodiment of the disclosed technique. With reference to FIG. 10A, a plurality of circular shaped CBs 422 are shown folded in an accordion-like or pleated manner. Sequential CBs are alternatively electrically coupled at the top and bottom (i.e., at opposite sides) of each CB with a flexible flat connection cable, shown as a plurality of flexible flat connection cables 424. Each flexible flat connection cable is long enough such that adjacent CBs can be folded one on top of the other with the flexible flat connection cable still having enough slack such that no mechanical stress is placed upon the flexible flat connection cable. Each one of plurality of circular shaped CBs 422 includes a plurality of electronic components 426.

According to the disclosed technique, optimal volume consumption of the configuration of electronic components shown is achieved by placing plurality of electronic components 426 on both sides of a CB. Optimal volume consumption relates to minimizing the amount of volume an electronic components configuration occupies. As shown, a circular shaped CB 428A includes electronic components on both sides. Optimal volume consumption is also achieved by the specific positioning of electronic components on a CB based on the dimensions (for example height) of each electronic component. For example, a CB 428A includes a relatively tall electronic component $430_1$ and a relatively short electronic component $432_1$ on one side and a relatively tall electronic component $430_2$ on its other side. A CB 428B also includes relatively tall electronic components (not labeled) and a relatively short electronic component $432_2$. Relatively tall electronic component $430_2$ is positioned on CB 428A such that when CB 428A is folded onto CB 428B, relatively tall electronic component $430_2$ from CB 428A will sit directly over relatively short electronic component $432_2$ from CB 428B. In this respect, electronic components on each CB are positioned based on their height such that when adjacent CBs are folded on top of one another, volume consumption is maximized by complementarily placing relatively tall electronic components over relatively short electronic components and vice-versa. As seen in FIG. 10A, when electronic components are positioned according to the disclosed technique, plurality of circular shaped CBs 422 can be folded up into a cylindrical shape while minimizing the volume required to encase the electronic components of each CB.

With reference to FIG. 10B, the encapsulation configuration of electronic components of FIG. 10A is shown, delineated by an arrow 452. Encapsulation configuration of electronic components 452 can now be encased in a protective cylinder 454. Protective cylinder 454 may be made from a metal, such as titanium, or from a plastic material. Protective cylinder has a relatively small diameter, and can have for example an inner diameter of 11 millimeters (herein referred to as mm). Encapsulation configuration of electronic components 452 may represent an electronics unit within an implantable medical device and may have a diameter which is smaller than 11 millimeters and a length which is less than 5 centimeters.

Figure 10C:
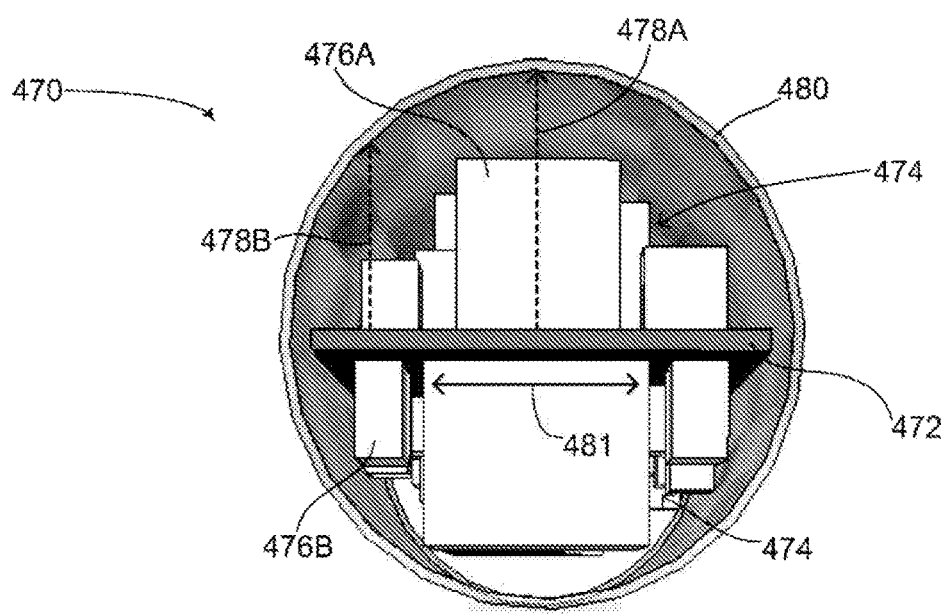
FIGS. 10C and 10D are schematic illustrations of another encapsulation configuration for electronic components in a flexible implantable medical device, constructed and operative in accordance with another embodiment of the disclosed technique.
Figure 10D:
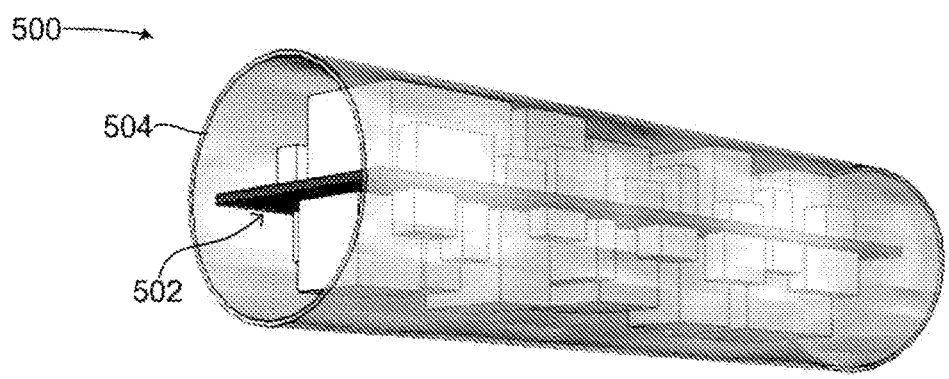

Reference is now made to FIGS. 10C and 10D, which are schematic illustrations of another encapsulation configuration for electronic components in a flexible implantable medical device, generally referenced 470 and 500 respectively, constructed and operative in accordance with another embodiment of the disclosed technique. With reference to FIG. 10C, a cross-sectional view of another encapsulation configuration for electronic components is shown. In this configuration, a single flat CB 472 is used to couple electronic components together. Flat CB 472 has a generally rectangular shape, being long and narrow. Flat CB 472 includes a plurality of electronic components 474, positioned on both sides of flat CB 472.

In FIG. 10C, optimal volume consumption of plurality of electronic components 474 is achieved by positioning taller electronic components, such as electronic component 476A along a center line (not shown) of flat CB 472, whereas shorter electronic components, such as electronic component 476B are positioned closer to the edges (not labeled) of flat CB 472. Flat CB 472 and plurality of electronic components 474 are encased in a protective cylinder 480. Protective cylinder 480 may be made from a metal, such as titanium, having an inner diameter of 11 millimeters (herein referred to as mm). As shown, the vertical distance between flat CB 472 and protective cylinder 480 various along a width 481 of flat CB 472. In the center (not labeled) of flat CB 472, the vertical distance is at a maximum, as shown by a dashed arrow 478A. As the edges of flat CB 472 are approached, the vertical distance approaches a minimum, as shown by a dashed arrow 478B. As understood by the worker skilled in the art, appropriate placing of the electronic components on flat CB 472 as described above can optimize the volume consumption of the electronic components in protective cylinder 480.

With reference to FIG. 10D, a perspective view of the encapsulation configuration for electronic components of FIG. 10C is shown. FIG. 10D includes a flat CB with a plurality of electronic components 502, as described above in FIG. 10C. Flat CB with plurality of electronic components 502 is encased in a protective cylinder 504. As seen optimal volume consumption by flat CB with plurality of electronic components 502 is achieved in protective cylinder 504 according to the disclosed technique.

Figure 10E:
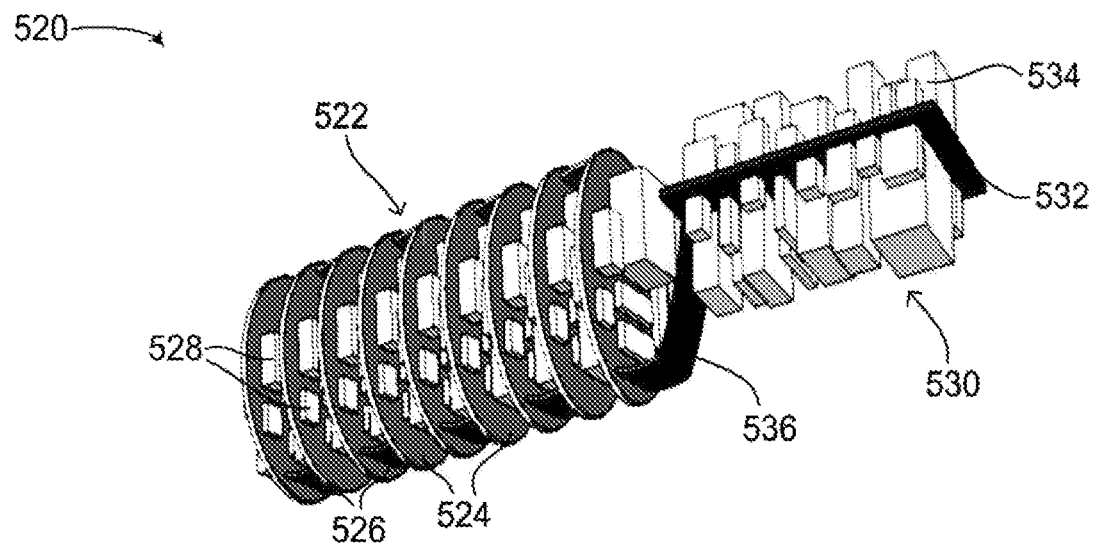
FIGS. 10E and 10F are schematic illustrations of a further encapsulation configuration for electronic components in a flexible implantable medical device, constructed and operative in accordance with a further embodiment of the disclosed technique.
Figure 10F:
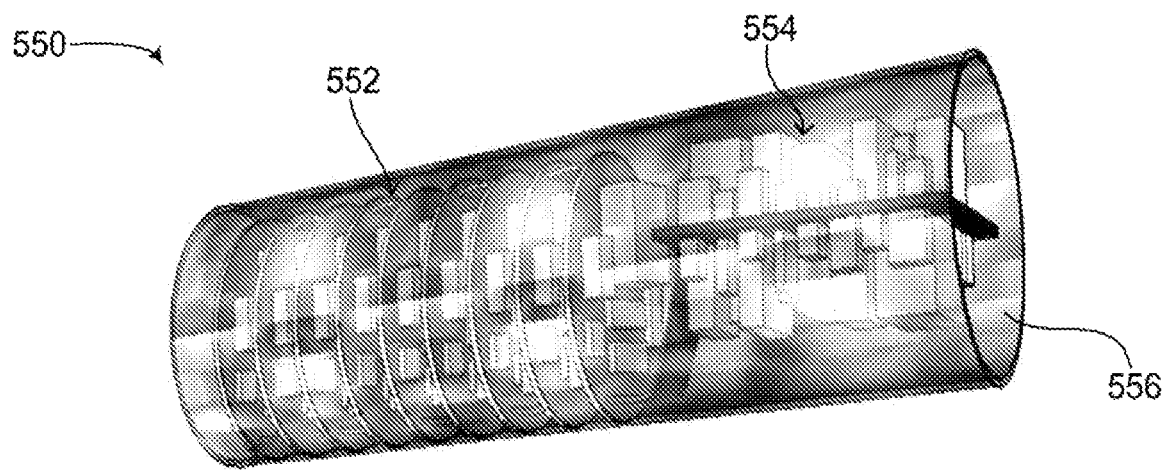

Reference is now made to FIGS. 10E and 10F, which are schematic illustrations of a further encapsulation configuration for electronic components in a flexible implantable medical device, generally referenced 520 and 550 respectively, constructed and operative in accordance with a further embodiment of the disclosed technique. With reference to FIG. 10E, encapsulation configuration for electronic components 520 is shown which substantially is a hybrid between the encapsulation configurations shown in FIGS. 10A-10B and 10C-10D. Encapsulation configuration for electronic components 520 includes a first section 522 wherein a plurality of flat CBs 524 are electrically coupled together sequentially at opposite ends of adjacent CBs by a plurality of flexible flat connection cables 526. A plurality of electronic components 528 are positioned on both sides of each of plurality of flat CBs 524 to achieve optimal volume consumption, as described above in FIGS. 10A and 10B. Encapsulation configuration for electronic components 520 also includes a second section 530 wherein a single rectangular shaped flat CB 532 includes a plurality of electronic components 534, positioned on both sides of flat CB 532 to achieve optimal volume consumption, as described above in FIGS. 10C and 10D. A longer flexible connection cable 536 electrically couples section 522 with section 530.

With reference to FIG. 10F, encapsulation configuration for electronic components 550 is shown including a first section 552 configured like section 522 (FIG. 10E) and a second section 554 configured like section 530 (FIG. 10E). Both first section 552 and second section 554 can be encased in a protective cylinder 556, thereby maximizing volume consumption of the electronic components in protective cylinder 556. As electronic components come in a variety of shapes and sizes, the advantage of the encapsulation configurations shown in FIGS. 10E and 10F is that generally smaller electronic components in a medical device can be positioned according to the configuration shown in the first sections (like in FIGS. 10A and 10B), where more electronic components may be positioned in a given volume, whereas generally larger electronic components in the medical device can be positioned according to the configuration shown in the second sections (like in FIGS. 10C and 10D), which affords more volume especially for tall electronic components.

Figure 11:
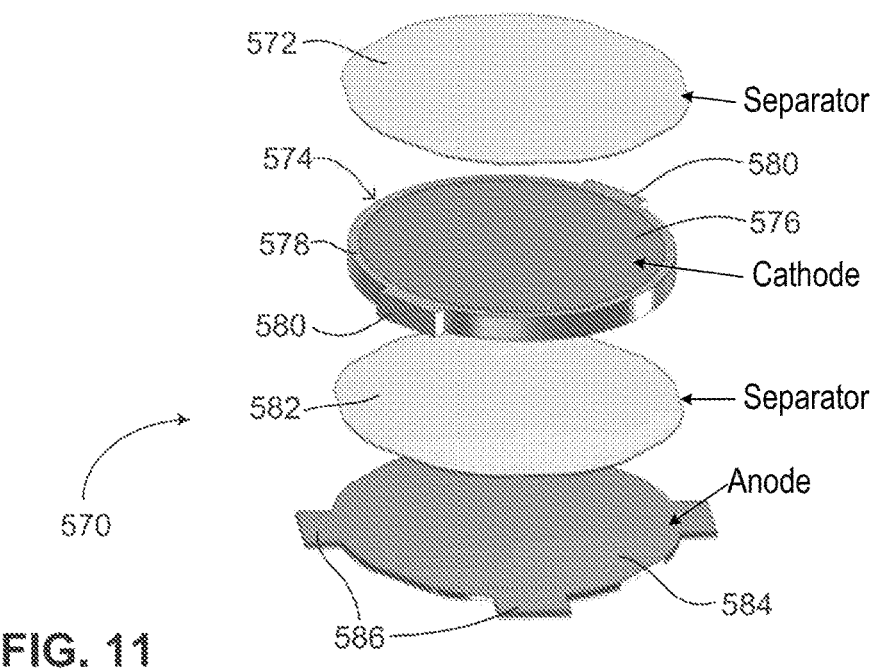
FIG. 11 is a schematic illustration of a single flat battery chip, shown in an exploded view, constructed and operative in accordance with another embodiment of the disclosed technique.
Figure 13:
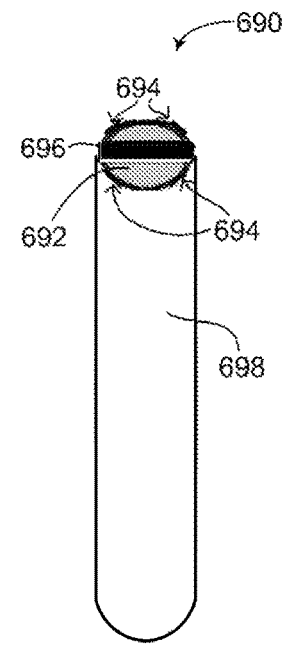
FIG. 13 is a schematic illustration of the plurality of single flat battery chips of FIG. 12 fully assembled into a battery, constructed and operative in accordance with another embodiment of the disclosed technique.

Reference is now made to FIG. 11, which is a schematic illustration of a single flat battery chip, shown in an exploded view, generally referenced 570, constructed and operative in accordance with another embodiment of the disclosed technique. FIG. 11 shows a single flat battery chip 570 in an exploded view. Single flat battery chip is not a functional battery but includes the necessary parts for building a battery. Single flat battery chip 570 includes a cathode 574 and an anode 584. The eventual battery chemistry as described below in FIG. 13 is able to produce high power and high current to enable charging a capacitor to around 1250 volts and around 70 joules of energy in under 12 seconds. In some embodiments of the disclosed technique, single flat battery chip 570 may be embodied as a three-dimensional thin film battery (herein referred to as 3D-TFB)

or a semi-3D-TFB, as disclosed in U.S. Pat. Nos. 6,197,450, 7,527,897, 7,618,748, reissued U.S. Pat. Nos. RE41,578 and RE42,073, and U.S. patent application Ser. No. 13/988,337. Single flat battery chip 570 can be combined with other single flat battery chips (not shown) as shown below in FIG. 12. Cathode 574 is covered by a first separator 572, while cathode 574 and anode 584 are separated by a second separator 582. First separator 572, cathode 574, second separator 582 and anode 584 are substantially circular in shape. Cathode 574 and anode 584 are made from known materials used for constructing cathodes and anodes. First separator 572 and second separator 582 are made from partially electrically insulating materials, such as porous polymers. Anode 584 includes four anode extensions 586. Anode 584 may include at least one anode current collector (not shown). Anode extensions 586 may be positioned anywhere along the circumference of anode 584. For example, anode extensions 586 are positioned approximately 90 degrees from one another. Anode 584 and anode extensions 586 may be coated with a current collector material, such as copper foil. Anode extensions 586 may have a thickness of approximately 20 microns. Cathode 574 includes a body 578, two cathode extensions 580 and an active cathode material 576. Cathode extensions 580 aid in cathode current collection, as described below. Active cathode material 576 may be incorporated into body 578 in a semi-3D-TFB or 3D-TFB configuration, as mentioned above. Active cathode material 576 may extend over to cathode extensions 580. Cathode 574 can act as its own current collector if conductive enough. Alternatively, cathode extensions 580 may serve as a cathode current collector as described below. Cathode 574 can include at least one cathode extension (not shown). The number of cathode and anode extensions can be equal (not shown) or unequal (as shown in FIG. 11A). Cathode extensions 580 may be positioned anywhere along the circumference of cathode 574. For example, cathode extensions 580 are positioned approximately 180 degrees from one another. Cathode extensions 580 and anode extensions 586 are positioned such that they do not overlap one another. Body 578 can be made from a hard material such as silicon or glass, for example in the form of a perforated silicon substrate or a glass capillary array (herein referred to as GCA). Active cathode material 576 may be made from any known cathode material, such as gold or the materials used in lithium ion batteries or lithium TFBs (see for example U.S. Pat. Nos. 6,197,450, 7,527,897, 7,618,748, reissued U.S. Pat. Nos. RE41,578 and RE42,073, and U.S. patent application Ser. No. 13/988,337. In another embodiment of the disclosed technique, body 578 may be made of a soft or flexible material such as a polymer, a plastic or rubber. Cathode extensions 580 are substantially thicker than anode extensions 586, and may be as thick as 500-1000 microns. Active cathode material 576 is deposited on body 578, which can be embodied as a perforated disc. First separator 572 and second separator 582 may be made from a porous polymer.

Figure 12:
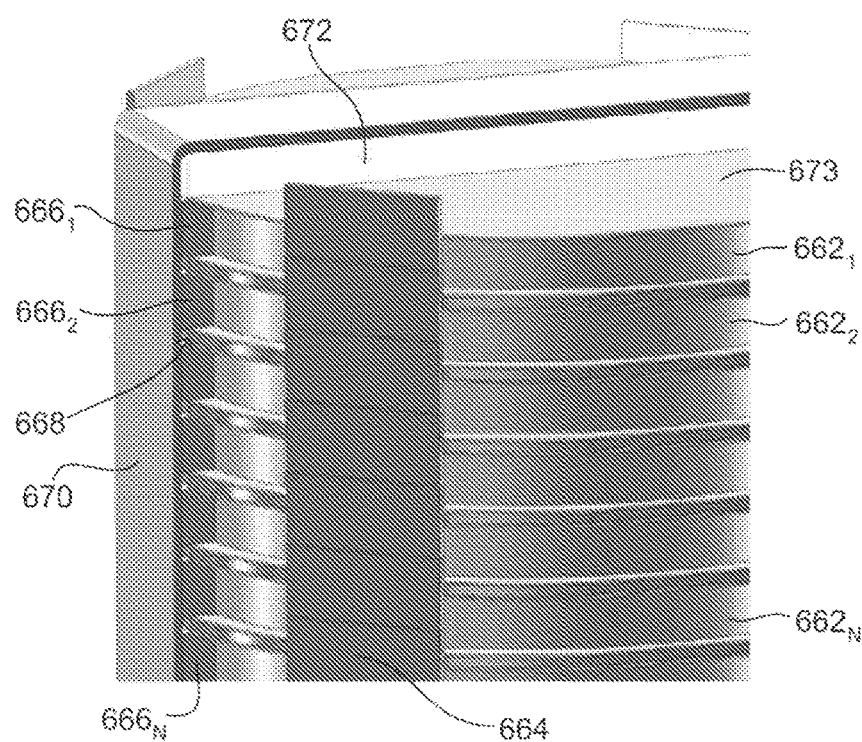
FIG. 12 is a schematic illustration of a plurality of single flat battery chips of FIG. 11, showing how the cathodes and anodes of each single flat battery chip are coupled together, constructed and operative in accordance with a further embodiment of the disclosed technique.

Reference is now made to FIG. 12, which is a schematic illustration of a plurality of single flat battery chips of FIG. 11, showing how the cathodes and anodes of each single flat battery chip are coupled together, constructed and operative in accordance with a further embodiment of the disclosed technique. As shown, a plurality of single flat battery chips 662$_1$, 662$_2$ and 662$_N$ are assembled together. All the anodes (not labeled) of each one of plurality of single flat battery chips 662$_1$, 662$_2$ and 662$_N$ are coupled together as shown by an arrow 664, to collect electrical current from the anodes. A plurality of cathode extensions 666$_1$, 666$_2$ and 666$_N$ are shown all lined up in parallel to one another. Plurality of cathode extensions 666$_1$-666$_N$ may be covered with a cathode current collector material. Due to the presence of separators (not labeled) between each cathode and anode of each single flat battery chip and the particular design of each cathode extension, a space exists between adjacent cathode extensions, such as a gap 668. In addition, the design of each cathode extension does not touch an adjacent anode (not labeled). As shown, plurality of cathode extensions 666$_1$, 666$_2$ and 666$_N$ are not electrically coupled to one another. In one embodiment, outside surfaces 661 of each cathode extension are covered with an electrically conductive coating, such as gold or nickel, so that each cathode extension is electrically coupled with the active cathode material of each single flat battery cell. In another embodiment, plurality of cathode extensions 666$_1$-666$_N$ are made from a conductive material and thus the plurality of cathode extensions are actually a plurality of cathode current collectors. In this embodiment, as in the previous embodiment, each cathode current collector is not electrically coupled with its neighboring cathode current collector.

As shown, each one of cathode extensions 666$_1$-666$_N$ can be coupled together using a collector band 670. Collector band 670 is made from a thin conductive metal which is substantially the width of a cathode extension. Collector band 670 wraps around the battery unit coupling cathode extensions on both sides of a single flat battery chip, thus enabling electrical current to flow from all the cathodes. Collector band 670 runs along the sides and top of the plurality of single flat battery chips. At the top of the plurality of single flat battery chips, an insulating rod 672 is placed on top of a first separator 673 of single flat battery chip 662$_1$ to prevent collector band 670 from making electrical contact with the anode (not labeled) of single flat battery chip 662$_1$. Collector band 670 thus substantially couples all the cathode extensions on each side of the plurality of single flat battery chips. As shown, all cathodes and anodes of the battery unit are coupled together, with all cathodes being electrically coupled via collector band 670 and all anodes being electrically coupled by four columns of anode extensions which touch one another. Thus each single flat battery chip is electrically coupled with its neighboring single flat battery chip in parallel. It is noted that the above description is based on the single flat battery chip of FIG. 11 in which the anode of a single flat battery chip is located underneath the cathode. The disclosed technique can also be embodied with the position of the cathode and anode in a single flat battery chip reversed, in other words, with the cathode of a single flat battery chip being located underneath the anode. This embodiment is not shown in the figures but the battery unit of the disclosed technique can be embodied as such. The structure of the plurality of single flat battery chips enable a plurality of battery chips to be coupled such that the anodes and the cathodes of each battery chip are respectively coupled together. As mentioned above, the structure shown in FIG. 12 is not a battery yet as it is lacking an electrolyte to enable current to flow through.

Reference is now made to FIG. 13, which is a schematic illustration of the plurality of single flat battery chips of FIG. 12 fully assembled into a battery, generally referenced 690, constructed and operative in accordance with another embodiment of the disclosed technique. Battery 690, once fully assembled as a plurality of single flat battery chips (not shown) is covered with a thin insulating sleeve 698, constructed from an electrically insulating material, such as non-conductive plastic. Thin insulating sleeve 698 may be rigid and may be used for assembling each single flat battery chip into battery 690. For example, the diameter of thin insulating sleeve 698 may be designed to securely hold each single flat battery chip in place while a second single flat battery chip is loaded into thin insulating sleeve 698, thus also preventing electrical shorts between single flat battery chips by preventing them from accidentally touching one another while being loaded into thin insulating sleeve 698. The diameter of thin insulating sleeve 698 may be less than the diameter of an anode (not shown) with its anode extensions (not shown) not folded such that placement of an anode inside thin insulating sleeve 698 causes the anode extensions to fold up sufficiently as shown in FIG. 12 to couple adjacent anode extensions to each other. Thin insulating sleeve 698 may also include a plurality of grooves (not shown) for lining up cathode extensions and anode extensions such that as single flat battery chips are loaded into thin insulating sleeve 698, cathode extensions and anode extensions form parallel columns, as shown in FIG. 12. As shown, only the top separator of the top single flat battery chip, a separator 692, is visible once thin insulating sleeve 698 has been loaded up with a plurality of single flat battery chips. Also visible are a plurality of tops 694 of the four anode extension columns (not shown) and a top part 696 of a collector band (not labeled) coupling the two cathode extension columns (not shown). Battery 690 may be placed inside a cylinder encasement (not shown). Electrical connections (not shown) can be made between plurality of tops 694 and top part 696 of the anode extensions and cathode extensions, therefore forming "plus" and "minus" terminals for battery 690. The cylinder encasement is then filled with an electrolyte (not shown) and fully sealed, thus constructing a fully functional battery (not shown). Battery 690 enables a relatively small sized battery of high power to be constructed. Unlike standard high power batteries which may include a plurality of lower power batteries coupled together, the embodiment shown in FIG. 13 enables high power generation in a single battery unit which includes a plurality of flat battery chips. This is possible due to the cathode and anode extensions of each flat battery chip and their respective configurations which enable adjacent cathodes and anodes to be electrically coupled with one another without each flat battery chip forming an individual battery or battery unit.

Figure 14:
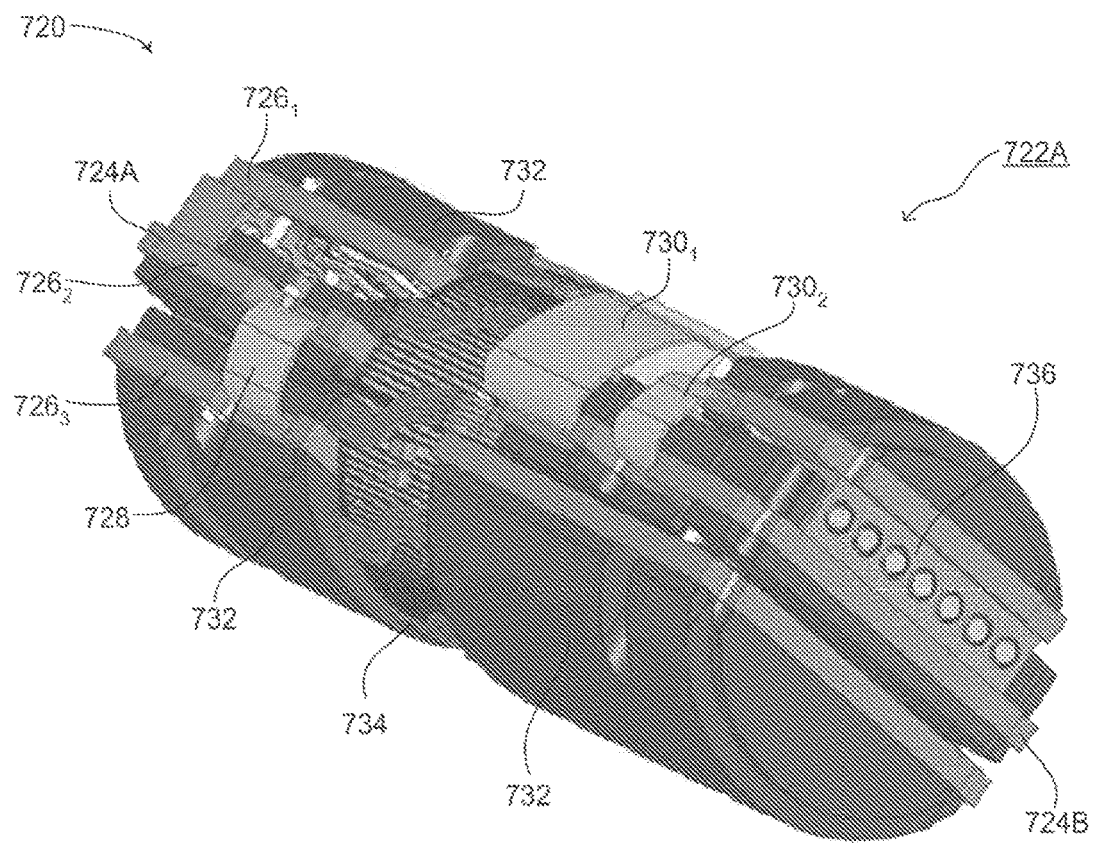
FIG. 14 is a schematic illustration of another encapsulation configuration for electronic components in a flexible implantable medical device, constructed and operative in accordance with a further embodiment of the disclosed technique.
Figure 14:
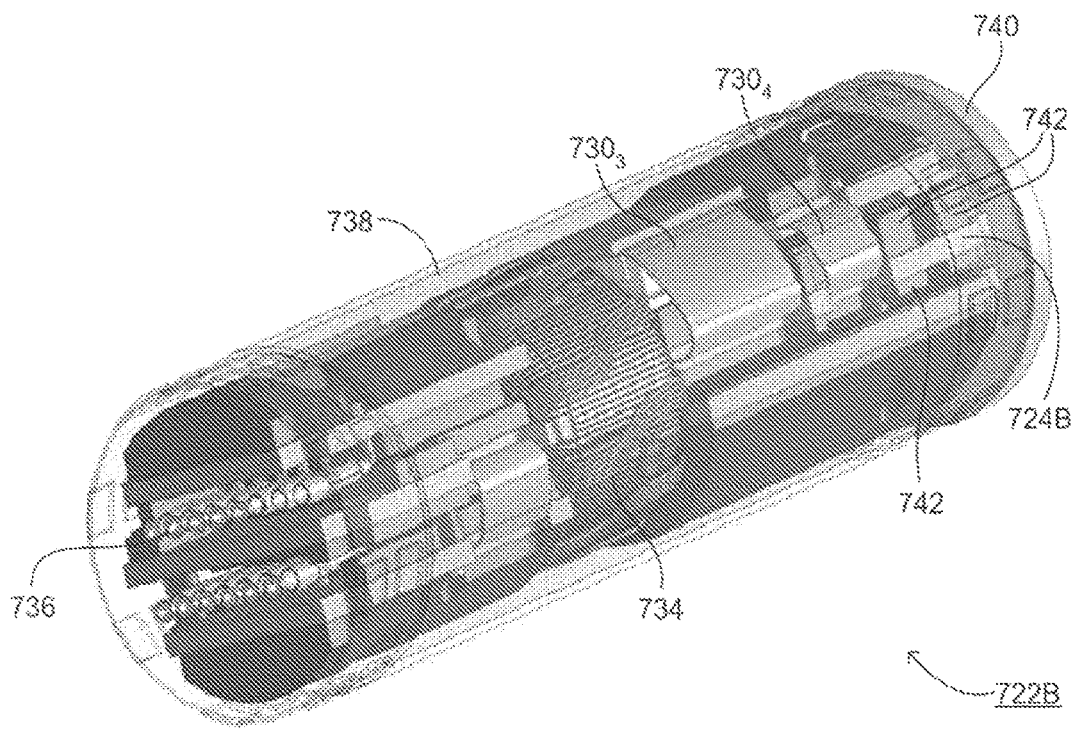

Reference is now made to FIG. 14, which is a schematic illustration of another encapsulation configuration for electronic components in a flexible implantable medical device, generally referenced 720, constructed and operative in accordance with a further embodiment of the disclosed technique. Encapsulation configuration 720 is shown in two views, a first view 722A and a second view 722B. Equivalent components in first view 722A and second view 722B are shown using identical reference numbers. With reference to first view 722A, shown is a first folded set of circuit boards, generally referenced 724A, which includes a plurality of circuit boards $726_1$, $726_2$ and $726_3$, coupled with via a flexible connection cable 728 and also via other similar flexible connection cables (not shown). Each one of circuit boards $726_1$, $726_2$ and $726_3$, includes a plurality of electronic components, such as transistors, capacitors, resistors and the like, similar to plurality of electronic components 474 (FIG. 10C). First folded set of circuit boards 724A may include at least one circuit board (not shown) or a plurality of circuit boards as shown (three in FIG. 14 although more or less circuit boards are possible). Each circuit board in first folded set of circuit boards 724A is generally shaped like a flat rectangle or square and is coupled on at least one side with a flexible connection cable, similar to the connected circuit boards shown above in FIGS. 9A, 9B, 10A and 10B. In FIG. 14, the circuit boards are folded over one another and lined up lengthwise as opposed to the widthwise placement of folded circuit boards one over the other as shown above in FIGS. 10A and 10B. The circuit boards are folded in a pleated manner, thereby giving the set of folded circuit boards an accordion-like shape or a stacked shape (such as plates stacked one on top of the other). Shown as well is a second folded set of circuit boards 724B having another arrangements of flexible connection cables. As shown, second folded set of circuit boards 724B has two flexible connection cables $730_1$ and $730_2$ on the same side. As is clear to the worker skilled in the art, other flexible connection cable arrangements are possible. Flexible connection cables 728, $730_1$ and $730_2$ can be embodied as flat connection cables.

A filler material 732 is used to cushion and protect first and second folded set of circuit boards 724A and 724B. Filler material 732 is shaped such that once all the circuit boards of first and second folded set of circuit boards 724A and 724B are covered and cushioned, first and second folded set of circuit boards 724A and 724B have a generally cylindrical shape. It is noted that if one of the folded set of circuit boards has many circuit boards, the upper and lower circuit boards may have different widths such that once folded and protected by filler material 732, the folded set of circuit boards maintains a generally cylindrical shape. Filler material 732 may be a hard plastic, a polymer or similar materials. Positioned between first and second folded set of circuit boards 724A and 724B is a transformer 734, which may be coupled with each folded set of circuit boards. Transformer 734 is an optional component and can be used to increase and decrease the voltages as might be required by the implantable medical device encapsulation configuration 720 is used with. As shown, transformer 734 is positioned widthwise as opposed to the folded set of circuit boards which are positioned lengthwise, making transformer 734 substantially orthogonal to first and second folded set of circuit boards 724A and 724B. Transformer 734 has a diameter substantially similar to the diameter of the cylindrical shape of the folded set of circuit boards, thus maximizing the space required to encapsulate the circuit boards and the transformer. As described above in FIGS. 10A, 10C and 10E, electronic components may be placed on the folded set of circuit boards in such as manner as to optimize the volume consumption the electronic components occupy on the circuit board once the circuit boards are folded over one another. For example, tall electronic components may be positioned over short electronic components when the circuit boards are folded, as shown above in FIG. 10A, or taller components may be placed more centrally in the circuit board with shorter components placed by the edges of the circuit board, as shown above in FIG. 10C. Shown as well in first view 722A is an electronic connector 736 for coupling the folded set of circuit boards with other electronic components, such as a battery, a processor, a capacitor and the like.

Encapsulation configuration 720 may be used with a variety of flexible implantable medical devices. For example, encapsulation configuration 720 can be used to include all the electronic components in an ICD, a CRT-D, a pacemaker, a pacing device and a monitoring device, except for the power source and any lead or leads required to provide electrical signals and/or sense signals in the body. In the case of a pacemaker (for pacing the heart), a pacing device (for pacing other body parts such as neurostimulators, brain pacemaker, gastric pacemakers and the like) and monitoring devices (for monitoring various signals in the body) where no amplification of voltage is necessary, transformer 734 is not needed. In such embodiments, encapsulation configuration 720 may include only one folded set of circuit boards, such as either first folded set of circuit boards 724A or second folded set of circuit boards 724B. In the case of ICDs, CRT-Ds and other implantable medical devices that require significant voltage amplification for functioning, encapsulation configuration 720 may include at least two folded sets of circuit boards and a transformer, for example as shown in FIG. 14. One folded set of circuit boards may include electronic components that function at a lower voltage whereas the other folded set of circuit boards may include electronic components that function at a higher voltage (as compared with the aforementioned lower voltage components). In this type of configuration, the transformer acts as the device which varies the voltage between the two folded sets of circuit boards.

With reference to second view 722B, second folded set of circuit boards 724B is shown with addition flexible connection cables 730$_3$ and 730$_4$. Transformer 734 is also shown as is electronic connector 736. Viewable in second view 722B is a plurality of electronic components 742, positioned on either side of one of the circuit boards (not labeled) of second folded set of circuit boards 724B. Second view 722B also shows a cover 738 for encapsulating and hermetically sealing first and second folded set of circuit boards. Cover 738 may be made from a polymer or another biocompatible material which is waterproof. Cover 738 is shown as an outline in FIG. 14 to enable the viewing of the components which it encapsulates. At least one of the ends of cover 738 may include a dielectric feed-through 740 for enabling the components inside cover 738 to be electronically coupled with other electronic components yet while remaining hermetically sealed.

Encapsulation configuration 720 can be used in a flexible implantable medical device as a link in a linked structure, with encapsulation configuration 720 being coupled with other similarly shaped components, such a cylindrically shaped battery or power source and/or a cylindrically shaped capacitor. In this manner, encapsulation 720 maximizes the volume occupied by the electronic components in a flexible implantable medical device. It will be appreciated by persons skilled in the art that the disclosed technique is not limited to what has been particularly shown and described hereinabove. Rather the scope of the disclosed technique is defined only by the claims, which follow.

The invention claimed is:

1. An encapsulation configuration for electronic components in a flexible implantable medical device, comprising:
at least one set of folded circuit boards; and
a filler material, wherein the filler material provides for cushioning and protecting the at least one set of folded circuit boards,
said at least one set of folded circuit boards comprising:
a plurality of circuit boards, each one of said plurality of circuit boards comprising at least one electronics component; and
a plurality of connection cables,
wherein each one of said plurality of circuit boards has a generally rectangular shape;
wherein each one of said plurality of connection cables electrically couples adjacent ones of said plurality of circuit boards; and
wherein said plurality of circuit boards are folded over one another in a pleated manner,
wherein said filler material surrounds said at least one set of folded circuit boards;
wherein said filler material is shaped such that said filler material and said at least one set of folded circuit boards together have a cylindrical shape, wherein the rectangular shaped circuit boards are sized so as to conform to the cylindrical shape once folded;
wherein said at least one set of folded circuit boards is positioned lengthwise in said cylindrical shape;
wherein the encapsulation configuration further comprises a cylindrically shaped transformer, coupled between a first one of said at least one set of folded circuit boards and a second one of said at least one set of folded circuit boards, said cylindrically shaped transformer being orthogonal in positioning to said lengthwise position of said at least one set of folded circuit boards; and
wherein said at least one electronics component is positioned on said at least one set of folded circuit boards to achieve optimal volume consumption once the circuit boards are folded over one another in said electronics encapsulation, wherein the optimal volume consumption is achieved by positioning taller ones of said at least one electronics component on a first one of said folded over circuit boards over shorter ones of said at least one electronics component on a second one of said folded over circuit boards.

2. The encapsulation configuration according to claim 1, further comprising a cover, for encasing said at least one set of folded circuit boards, wherein said at least one set of folded circuit boards is inserted lengthwise into said cover.

3. The encapsulation configuration according to claim 2, said cover further comprising at least one dielectric feed-through.

4. The encapsulation configuration according to claim 1, further comprising an electronic connector for electronically coupling said at least one set of folded circuit boards with at least one other electronic component in said flexible implantable medical device.

5. The encapsulation configuration according to claim 1, wherein said at least one electronics component is selected from the list consisting of:
capacitors;
resistors;
transistors;
switches;
processors;
transformers;
diodes;
application specific integrated circuits; and
field-programmable gate arrays.

6. The encapsulation configuration according to claim 1, wherein said plurality of connection cables is flexible.

7. The encapsulation configuration according to claim 1, each one of said plurality of circuit boards comprising said at least one electronics component on at least one side of said respective one of said plurality of circuit boards.

8. The encapsulation configuration according to claim 1, wherein said filler material is constructed from a material selected from the list consisting of:
polymer; and
hard plastic.

9. The encapsulation configuration according to claim 1, wherein said flexible implantable medical device is selected from the list consisting of:
an implantable cardioverter defibrillator (ICD);
a pacemaker;
a pacing device; and
a monitoring device.

10. An encapsulation configuration for electronic components in a flexible implantable cardioverter defibrillator (ICD), comprising:
- at least two sets of folded circuit boards;
- a cylindrically shaped transformer; and
- a filler material,
- each one of said at least two sets of folded circuit boards comprising:
- a plurality of circuit boards, each one of said plurality of circuit boards comprising at least one electronics component, wherein a first of the at least two sets of folded circuit boards functions at a lower voltage than a second of at least two sets of folded circuit boards and wherein the cylindrically shaped transformer varies the voltage between the first and the second of the at least two sets of folded circuit boards;
and
- a plurality of connection cables,
- wherein each one of said plurality of circuit boards has a generally rectangular shape;
- wherein each one of said plurality of connection cables electrically couples adjacent ones of said plurality of circuit boards; and
- wherein said plurality of circuit boards are folded over one another in a pleated manner,
- wherein said transformer is positioned orthogonally between a first one of said at least two sets of folded circuit boards and a second one of said at least two sets of folded circuit boards;
- wherein said filler material surrounds each one of said at least two sets of folded circuit boards;
- wherein said filler material is shaped such that said filler material, said transformer and said at least two sets of folded circuit boards together have a cylindrical shape, wherein said transformer has a diameter substantially similar to the diameter of the cylindrical shape, wherein the rectangular shaped circuit boards are sized so as to conform to the cylindrical shape once folded;
- wherein said at least two sets of folded circuit boards are positioned lengthwise in said cylindrical shape, orthogonally to said transformer; and
- wherein each one of said at least one electronics component is positioned on each one of said at least two sets of folded circuit boards to achieve optimal volume consumption once the circuit boards are folded over one another in said electronics encapsulation, wherein the optimal volume consumption is achieved by positioning taller ones of said at least one electronics component on a first one of said folded over circuit boards over shorter ones of said at least one electronics component on a second one of said folded over circuit boards.

11. The encapsulation configuration according to claim 10, further comprising a cover, for encasing said at least two sets of folded circuit boards and said cylindrically shaped transformer, wherein said at least two sets of folded circuit boards are inserted lengthwise into said cover and said cylindrically shaped transformer is inserted widthwise into said cover.

12. The encapsulation configuration according to claim 11, said cover further comprising at least one dielectric feed-through.

13. The encapsulation configuration according to claim 10, further comprising an electronic connector for electronically coupling at least one of said at least two set of folded circuit boards with at least one other electronic component in said flexible ICD.

14. The encapsulation configuration according to claim 10, wherein said at least one electronics component is selected from the list consisting of:
- capacitors;
- resistors;
- transistors;
- switches;
- processors;
- transformers;
- diodes;
- application specific integrated circuits; and
- field-programmable gate arrays.

15. The encapsulation configuration according to claim 10, wherein said plurality of connection cables is flexible.

16. The encapsulation configuration according to claim 10, wherein said filler material is constructed from a material selected from the list consisting of:
- polymer; and
- hard plastic.

* * * * *